United States Patent [19]

Hight et al.

[11] Patent Number: 5,464,636
[45] Date of Patent: Nov. 7, 1995

[54] BIOCIDAL METHODS AND COMPOSITIONS FOR RECIRCULATING WATER SYSTEMS

[75] Inventors: Terry V. T. Hight; Jack V. Matson, both of Houston, Tex.; Lawrence F. Rakestraw, Chesterfield, Mo.; Zhihe Zhang, Houston, Tex.; Thomas C. Kuechler, St. Louis, Mo.

[73] Assignee: The University of Houston, Houston, Tex.

[21] Appl. No.: 212,287

[22] Filed: Mar. 14, 1994

Related U.S. Application Data

[63] Continuation of Ser. No. 750,744, Aug. 21, 1991, abandoned, which is a continuation of Ser. No. 366,936, Jun. 16, 1989, abandoned.

[51] Int. Cl.$^6$ .................................................. A01N 43/50
[52] U.S. Cl. .................... 424/661; 424/723; 514/241; 514/247; 514/387; 514/389
[58] Field of Search ................................. 424/661, 723; 514/241, 247, 389, 387

[56] References Cited

U.S. PATENT DOCUMENTS

| | | | |
|---|---|---|---|
| 2,815,311 | 12/1957 | Ellis | 167/18 |
| 3,035,056 | 5/1962 | Symes et al. | 260/248 |
| 3,035,057 | 5/1962 | Symes et al. | 260/248 |
| 3,147,219 | 9/1964 | Paterson | 210/62 |
| 3,150,132 | 9/1964 | Symes et al. | 260/248 |
| 3,152,073 | 10/1964 | Morton | 210/62 |
| 3,256,199 | 6/1966 | Symes et al. | 252/99 |
| 3,294,797 | 12/1966 | Shallenberger | 260/248 |
| 3,364,146 | 1/1968 | Casey et al. | 252/99 |
| 3,412,021 | 11/1968 | Paterson | 210/62 |
| 3,846,324 | 11/1974 | Lohmann et al. | 25/95 |
| 3,876,768 | 4/1975 | Blank | 42/128 |
| 3,931,213 | 1/1976 | Kaminski et al. | 26/307 |
| 3,975,271 | 8/1976 | Saunier et al. | 210/62 |
| 4,000,293 | 12/1976 | Kaminski et al. | 42/272 |
| 4,119,535 | 10/1978 | White et al. | 210/62 |
| 4,241,080 | 12/1980 | Burk | 424/304 |
| 4,297,224 | 10/1981 | Macchiarolo et al. | 210/755 |
| 4,300,897 | 11/1981 | Gray | 8/111 |
| 4,411,799 | 10/1983 | Ito et al. | 210/753 |
| 4,451,376 | 5/1984 | Sharp | 210/701 |
| 4,489,098 | 12/1984 | Relenyi et al. | 424/333 |
| 4,557,926 | 12/1985 | Nelson et al. | 424/661 |
| 4,661,344 | 4/1987 | Relenyi | 424/79 |
| 4,698,165 | 10/1987 | Theyson | 210/755 |
| 4,755,354 | 7/1988 | Trinh et al. | 422/37 |
| 4,759,852 | 7/1988 | Trulear | 210/699 |
| 4,767,542 | 8/1988 | Worley | 21/755 |
| 4,846,979 | 7/1989 | Hamilton | 210/754 |
| 5,000,869 | 3/1991 | Dittert | 25/174 |
| 5,019,380 | 5/1991 | Heiler | 42/81 |
| 5,049,385 | 9/1991 | Wiedrich et al. | 42/408 |

FOREIGN PATENT DOCUMENTS

| | | |
|---|---|---|
| 1126432 | 11/1956 | France . |
| 2042254 | 3/1971 | Germany . |
| 1196870 | 7/1970 | United Kingdom . |
| 1327531 | 8/1973 | United Kingdom . |
| 1358617 | 7/1974 | United Kingdom . |

OTHER PUBLICATIONS

Matson, et al., "Biofouling Control in Recycled Cooling Water with Bromo Chloro Dimethylhydantoin," Cooling Tower Institute, 1982 Annual Meeting (Feb. 1, 1982).
White, The Handbook of Chlorination, 2d ed., Van Nostrand Reinhold Co., N.Y. (1969).
Holzwarth, et al., "The Fate of Chlorine and Chloramines in Cooling Towers–Henry's Law Constants for Flashoff," Water Res., vol. 18, No. 11, pp. 1421–1427 (1984).
Shere, et al., "Effect of Bromide–Hypochlorite Bactericides on Microorganisms," Applied Microbiology, vol. 10, 538–41 (1962).
Petterson, et al., "N–Halogen Compounds. II. The N–Cl Stretching Band in Some N–Chloroamides. The Structure of Trichloroisocyanuric Acid," The Journal of Organic Chemistry, vol. 25, No. 9, pp. 1595–1598 (1960).
Nelson, et al., "ACL Technology for Residential Spas and Hot Tubs," Monsanto Technology, report No. MSL 1233, (1980).
Nelson, "Swimming Pool Disinfection With Chlorinated–S–Triazine Trione Products," Monsanto Industrial Chemicals Company Special Report No. 6862, revised May, 1975, FIG. 49, Effect of Cyanuric Acid, pH and Glycoluril on the Stability of Hypochlorite Exposed to Sunlight.
Chemical Abstract (73:80491f) 1970 McCullins.
Chemical Abstracts (66:121597w) 1967 Gotterli.

Primary Examiner—Raymond Henley, III
Assistant Examiner—K. Weddington

[57] ABSTRACT

Improved biocidal composition and method for controlling biofouling and microorganism population levels in recirculating water systems such as cooling towers, swimming pools or spas is disclosed and claimed. The composition comprises a hypochlorite donor and a bromide ion donor in proportions selected to maintain a mole ratio of the sum of all bromine containing species to the sum of all hypohalite species in the recirculating water of about 0.2 to about 20. The method comprises introducing into the recirculating water a mixture or combination of a hypochlorite donor and a bromide ion donor in an amount sufficient to maintain a ratio of the sum of all bromine containing species to the sum of all species in the recirculating water in the range of about 0.2 to about 20. In addition, a bromine volatilization suppressant may be introduced into the recirculating water to inhibit loss of bromide ion through volatilization of bromine containing species formed by reaction of the hypochlorite donor and the bromide ion donor. One or more scale inhibitors and compacting aids may also be added.

71 Claims, 4 Drawing Sheets

BIOCIDAL METHODS AND COMPOSITIONS FOR RECIRCULATING WATER SYSTEMS

This application is a continuation of application Ser. No. 07/750,744, filed Aug. 21, 1991, now abandoned which is a continuation of application Ser. No. 366,936, filed Jun. 16, 1989; now abandoned.

BACKGROUND OF THE INVENTION

1. Field of the Invention

This invention relates to the disinfection of water and to the control of biofouling in recirculating water systems such as cooling towers, evaporative condensers, air washers, swimming pools, hot tubs, and spas.

The invention more especially concerns methods and compositions for controlling biofouling and microorganism population levels in such systems wherein water soluble hypochlorite donors and bromide ion donors are added to the systems so as to improve biocidal effectiveness with reduced costs.

As used herein, the term "hypochlorite donor" means any compound that will generate hypochlorite species when dissolved in water.

The term "bromide ion donor" means any compound that will generate bromide ions when dissolved in water.

The term "available halogen" means the standard form for expressing the strengths or capacities of halogenating chemicals as well as for the doses in which they are applied and for the hypohalite species (HOCl, OCl$^-$, HOBr, OBr$^-$) which remain in the water.

The term "available chlorine" means the same as "available halogen", but refers specifically to chlorine compounds.

The term "available bromine" means the same as "available halogen", but refers specifically to bromine compounds.

The term "hypohalite species" means hypochlorous acid, hypochlorite ion, hypobromous acid and hypobromite ion.

The term "hypochlorite species" means hypochlorous acid and hypochlorite ion.

The term "hypobromite species" means hypobromous acid and hypobromite ion.

The term "bromine species" means hypobromous acid, hypobromite ion, and bromide ion.

The terms "free halogen" and "free available halogen" are used interchangeably and are defined as the concentration of halogen existing in the water as hypohalous acid, HOX, and hypohalite ion, OX$^-$, where X is Cl or Br.

The terms "free chlorine" and "free available chlorine" are used interchangeably and are defined as the concentration of chlorine existing in the water as hypochlorous acid, HOCl, and hypochlorite ion, OCl$^-$.

The terms "free bromine" and "free available bromine" are used interchangeably and are defined as the concentration of bromine existing in the water as hypobromous acid, HOBr, and hypobromite ion, OBr$^-$.

The terms "combined halogen" and "combined available halogen" are used interchangeably and are defined as the concentration of halogen existing in the water in chemical combination with ammonia or organic nitrogen compounds.

The terms "combined chlorine" and "combined available chlorine" are used interchangeably and are defined as the concentration of chlorine existing in the water in chemical combination with ammonia or organic nitrogen compounds.

The terms "combined bromine" and "combined available bromine" are used interchangeably and are defined as the concentration of bromine existing in the water in chemical combination with ammonia or organic nitrogen compounds.

The terms "total halogen" and "total available halogen" are used interchangeably and are defined as the sum of "free halogen" (or "free available halogen") and "combined halogen" (or "combined available halogen").

The terms "total chlorine" and "total available chlorine" are used interchangeably and mean the same as "total halogen" and "total available halogen" but specifically refer to chlorine.

The terms "total bromine" or "total available bromine" are used interchangeably and mean the same as "total halogen" and "total available halogen" but specifically refer to bromine.

The symbol "FAvC" represents "free chlorine" and "free available chlorine" concentrations in the water.

The symbol "AvC" represents the available chlorine content of the hypochlorite donor.

The term "halogen demand" is defined as the amount of halogen which must be added to the water over a specific period of time to maintain the "free halogen" and/or "free available halogen" at a specific concentration in the water.

The term "chlorine demand" means the same as the "halogen demand" but specifically refers to "free chlorine" and/or "free available chlorine" concentrations.

The term "chlorinated isocyanuric acid derivative" means chlorinated isocyanuric acid including dichlorinated and trichlorinated isocyanuric acid, alkali metal and alkaline earth metal salts of chlorinated isocyanuric acid, and hydrates, complexes and mixtures thereof.

The term "hydantoin derivative" means an unsubstituted, halogenated (i.e. chlorinated or brominated), or alkylated hydantoin.

The term "sulfamic acid derivative" means unsubstituted, halogenated, or alkylated sulfamic acid.

The term "sulfonamide derivative" means halogenated, alkylated, or arylated sulfonamide.

The term "glycoluril derivative" means unsubstituted, halogenated, or alkylated glycoluril.

The term "succinimide derivative" means unsubstituted, halogenated, or alkylated succinimide.

The term "oxazolidinone derivative" means an unsubstituted, halogenated, alkylated, or arylated oxazolidinone.

The term "imidazolidinone derivative" means an unsubstituted, halogenated, alkylated, or arylated imidazolidinone.

The term "halogen concentration (free chlorine basis or free available chlorine basis)" means the halogen concentration in terms of free available chlorine, regardless of whether the halogen species are hypochlorite, hypobromite or mixtures thereof.

2. Related Art

Cooling towers are used to provide cooling for the air conditioning systems of office buildings, hotels and hospitals and to provide cooling for industrial processes. The water in these towers is subject to contamination from the air blown through the tower and from the fresh water used to compensate for evaporative losses and blowdown. The contamination consists of both inorganic and organic debris as well as live microorganisms capable of growing and multiplying if suitable conditions are provided. Formation of microbial deposits, known as biofouling, can occur on almost any surface exposed to an aqueous environment, causing substantial energy losses due to increased heat transfer resistance. For this and other reasons, cooling towers are adversely affected by microorganisms, e.g. bacteria, fungi, molds, and algae, by either sheer numbers of organisms, metabolic waste products generated, health hazards presented, or deposits created. Unfortunately, cooling towers provide many of the conditions ideal for microbial growth, namely favorable temperatures and moisture levels, and favorable concentrations of air and nutrients.

Air washers are used to cool, cleanse, and humidify the air in office buildings, factories, shopping malls, and the like. Due to the large amount of air drawn through the water, the growth of microorganisms is again a problem. Since the air is used directly for inhabited areas, the toxicity and odor of any compounds used for treatment of the water in the air washers must be extremely low.

Similarly, water in swimming pools, hot tubs and spas must be sanitized in order to control disease spreading microorganisms. As with air washers, the toxicity and odor of compounds used to treat the water must be extremely low.

It is customary to treat biologically contaminated water with one or more biocides to control the population of microorganisms in the water, to prevent fouling of heat exchanger surfaces, and to prevent the spread of disease. The biocides most commonly used to disinfect and sanitize water in recirculating water systems are chemicals that generate hypochlorite species when dissolved in water. There are many hypochlorite generating chemicals, but the more common ones are chlorine gas, alkali metal hypochlorites such as sodium hypochlorite, alkaline earth metal hypochlorites such as calcium hypochlorite, chlorinated hydantoins, and chlorinated isocyanuric acid derivatives.

Dry sources of biocide are often preferable to gaseous or even liquid forms because the dry forms are often safer to handle, more convenient to store and use, and more stable in storage. Moreover, one or more dry products may conveniently be fed to a recirculating water system using an erosion feeder in which water is passed through a bed of solid biocide to slowly dissolve the biocide and is then added to the recirculating water. One such erosion feeder is described in U.S. Pat. No. 3,412,021.

The different forms of hypochlorite donors all work by generating hypochlorous acid (HOCl) in solution, which provides the significant biocidal action. Hypochlorous acid has strong biocidal properties under the proper conditions. Its killing power is adversely affected, however, by alkaline pH levels and by the presence of ammonia or other nitrogenous material.

The pH of cooling water is typically regulated in the range of 8.0 to 9.0 for alkaline corrosion protection. At pH levels above 7.5, chlorine-based biocides become less effective because of the equilibrium shift from hypochlorous acid to hypochlorite ion.

$$HOCl \leftrightarrows OCl^- + H^+ \quad (1)$$

$$pK = -\log\left[\frac{[OCl^-][H^+]}{[HOCl]}\right] = 7.5 \text{ (at } 20° \text{ C.)}$$

The hypochlorite ion cannot easily penetrate microorganism cell membranes, while the uncharged hypochlorous acid can passively diffuse into cells to cause damage.

Water in recirculating water systems is also frequently contaminated with ammonia due to the decomposition of nitrogenous impurities in the water or to the leakage of ammonia from refrigeration units into the cooling water. Ammonia or chloramines are also commonly introduced into the recirculating water system by the makeup water. Hypochlorite species react with ammonia to form chloramines. Since chlorine is bound very strongly by nitrogen, the chlorine is not readily released by chloramines to the water as hypochlorite species, and the biocidal activity of the chlorine-based biocide is, therefore, greatly reduced. The fact that the chloramines are relatively stable chlorine compounds also makes it more difficult for some cooling tower systems to comply with the EPA total halogen (free halogen+combined halogen) discharge limit of 0.2 ppm. In some cases, these cooling tower systems frequently have to dechlorinate the discharge water in order to be in compliance. Moreover, chloramines have a disagreeable and irritating odor. They can be converted to odorless nitrogen gas by maintaining the appropriate free chlorine concentration in the recirculating water, but some chloramines are still volatilized into the air. Even though the amounts are negligible, chloramine odors are still noticeable. Chloramine odor is an important issue with indoor pools and spas because the air containing the volatilized chloramines is retained in the buildings long enough for the chloramine concentration to accumulate to levels that are objectionable to the consumer. Thus, the formation of chloramines in recirculating water can present a serious obstacle to the use of chlorine-based biocides.

Hypobromous acid (HOBr), which can be generated from a number of compounds including liquid bromine and N-bromo organic compounds or by reacting a bromide salt with a solution of hypochlorous acid or other oxidizing agents, is a more effective biocide on a molar basis than hypochlorous acid. Under some conditions, this superiority is quite dramatic. In particular, hypobromous acid is known to react with ammonia to produce bromamines. Bromamines, unlike chloramines, have very good biocidal activity and have a more acceptable odor. Bromamines also have a distinct advantage over chloramines because they dissipate more readily, thereby making it easier to operate cooling towers in compliance with the EPA limits for total halogen. In addition, hypobromite species are more effective than hypochlorite species at pH values above 7.5 due to the higher pK value for the equilibrium shift from hypobromous acid to hypobromite ion.

$$HOBr \leftrightarrows OBr^- + H^+ \quad (2)$$

$$pK = -\log\left[\frac{[OBr^-][H^+]}{[HOBr]}\right] = 8.5 \text{ (at } 20° \text{ C.)}$$

In most cases where hypobromous acid is used as a biocidal agent, the hypobromous acid generating composition contains a large weight percentage of bromine. Liquid bromine, for example, is 100% bromine by weight and 1-bromo-3-chloro-5,5-dimethylhydantoin (BCDMH) is 32.8% bromine by weight. This practice leads to higher costs for the bromine-based biocides since the cost of bromine is about three times the cost of chlorine per pound. Since 2.25 pounds of bromine contain the same number of moles of available halogen as only 1.0 pound of chlorine, bromine is over seven times more expensive than chlorine on a per mole basis. Even though hypobromous acid is generally superior to hypochlorous acid, the higher cost of bromine has limited the use of bromine-based biocides.

Nevertheless, in the past few years several products have been introduced into the cooling tower marketplace which take advantage of the bromine chemistry. In 1982, Nalco introduced a bromine-based product (tradename Actibrom) for use in large scale cooling towers. These towers already had chlorinators injecting gaseous chlorine for disinfection. Actibrom is simply an aqueous solution of sodium bromide, and is typically added in proportion to the chlorine gas using a separate feeder. See U.S. Pat. No. 4,451,376. Another bromine-based biocide, 1-bromo-3-chloro-5,5-dimethylhydantoin (BCDMH) was introduced into the cooling tower marketplace by Great Lakes Chemical. See U.S. Pat. No. 4,297,224.

Bromine sanitizers have also gained some measure of popularity for indoor pool and spa applications, because the odor of the bromamines, formed by reaction of hypobromite species with nitrogenous wastes, is less objectionable to the consumer. Bromine sanitizers, however, have not been popular for outdoor pools because the hypobromite species are rapidly dissipated in sunlight and the sanitizer costs are considerably higher than chlorine sanitizers with cyanuric acid.

Potassium monopersulfate and sodium bromide have been marketed together as a bromine sanitizer system for spa applications. The recommended practice is to dose the spa water with sodium bromide (usually as a solution) and then add the recommended dosages of potassium monopersulfate as needed. Hypobromous acid is generated by oxidation of the bromide ion with persulfate ions as shown by the following equation:

$$KHSO_5 \cdot KHSO_4 + NaBr \rightarrow HOBr + KHSO_4 + NaKSO_4 \quad (3)$$

Currently available dry sources of hypobromous acid suffer from a number of disadvantages in addition to their higher cost. The hydantoin products such as BCDMH, 1,3-dichloro-5,5-dimethylhydantoin (CCDMH), 1,3-dibromo-5,5-dimethylhydantoin (BBDMH), 1,3-dichloro-5-ethyl-5-methylhydantoin (CCEMH), and 1-bromo-3-chloro-5-ethyl-5-methylhydantoin (BCEMH) have very low dissolution rates which necessitates the use of large feeder systems and high water flow rates. Moreover, in some cases it is desirable to add a large amount of available halogen at one time to rapidly clean up a recirculating water system. This is known as a "shock treatment". Such a treatment would be desired whenever a system has experienced a large amount of contamination or when microorganism growth has gotten out of control. However, the hydantoin products are generally unsuited for this application due to their low dissolution rates.

In addition, the hydantoin products are not as effective biocides as might be expected based on the amount of hypobromous acid formed, because these products also release large amounts of 5,5-dimethylhydantoin (DMH) or 5-ethyl-5-methylhydantoin (EMH) into the water, eventually leading to the buildup of high concentrations of DMH or EMH in the water. High concentrations of DMH or EMH inhibit the biocidal activity of the hypobromous acid by virtue of the following equilibria:

$$HOBr + DMH \rightleftharpoons H_2O + BDMH \quad (4)$$

$$HOBr + EMH \rightleftharpoons H_2O + BEMH \quad (5)$$

where BDMH is bromo-DMH and BEMH is bromo-EMH. This effect has previously been noted in U.S. Patent 4,698,165.

As an alternative to the hydantoins, hypobromous acid may be prepared by reacting a bromide salt with a source of hypochlorite species according to the following equation:

$$HOCl + Br^- \rightarrow HOBr + Cl^- \quad (6a)$$

$$OCl^- + Br^- \rightarrow OBr^- + Cl^- \quad (6b)$$

as previously taught, for example, in British Patent 1,327,531 and U.S. Pat. Nos. 2,815,311; 3,975,271; and 4,119,535. The hypobromous acid formed by the above equation is the active biocide. However, in the process of killing microorganisms or oxidizing organic material, the hypobromous acid is reduced to form bromide ion, as shown by the following equation:

$$HOBr + microorganisms \rightarrow dead\ microorganisms + Br^- + H_2O \quad (7)$$

Thus, the bromide ion can be reused to generate more hypobromous acid by reaction with hypochlorite species as shown above in equations 6a and 6b. Because the bromide ion is continuously reused, only small amounts of bromide ion are necessary to make a chlorine-based biocide in combination with bromide salts perform as a bromine biocide.

Some prior art teaches that, when using mixtures of chlorine-based biocides in combination with bromide salts, large excesses of bromide ion should be maintained in the recirculating water. For example, British Patent No. 1,327,531 describes a process for sanitizing swimming pool water wherein the concentration of bromide is maintained at 20 to 50 mg per liter (expressed as sodium bromide) and the concentration of the hypobromite species is maintained at 0.4 mg/L. Other prior art, e.g., U.S. Pat. No. 3,975,271, suggests that when hypobromous acid is generated by reacting a bromide salt with a source of hypochlorous acid, the optimum mole ratio of chlorine to bromide is near 1. However, no information is provided as to how to maintain the ratio near the optimum in the recirculating water while chlorine and bromide salts are being fed simultaneously to the system as well as being lost from the system.

SUMMARY OF THE INVENTION

This invention is broadly concerned with compositions and methods for controlling biofouling and microorganism population levels in recirculating water systems using compositions or combinations of hypochlorite donors and bromide ion donors.

The proportion of hypochlorite donor and bromide ion donor in the composition or combination added to the system is selected to maintain an optimum ratio of all bromine containing species to the sum of all hypohalite species in the recirculating water. It has now been found that significant amounts of bromide ion are lost from recirculating water systems through the pathways of volatilization of hypobromous acid and bromamines and of formation of stable organobromine compounds. Moreover, hypochlorite species, hypobromite species, and bromide ion are lost from the recirculating water at different rates. These loss rates must be known in order to prescribe at what rates to feed the hypochlorite donor and bromide ion donor to the water to compensate for the losses and maintain the desired steady state concentrations.

It is very important, therefore, to control the chemistries of the reactions of the hypochlorite species with the bromide ion (equations 6a and 6b) in a dynamic system. More specifically, it is critical to control the mole ratio of the sum of all bromine-containing species (HOBr, OBr$^-$ and Br$^-$) to the sum of all hypohalite species (HOBr, OBr$^-$ HOCl and OCl$^-$) present in the water. For the purposes of this discussion, this mole ratio will be referred to herein as the "chlorine-to-bromine conversion ratio" or "Conversion Ratio" ("CR") and will be written as:

$$CR = \frac{\text{moles of (HOBr + OBr}^- + \text{Br}^-)}{\text{moles of (HOBr + OBr}^- + \text{HOCl + OCl}^-)}$$

This ratio will be used hereafter because it is a convenient way to express the instantaneous measure of the extent of conversion of the hypochlorite species to hypobromite species. It is also a convenient way to establish if the hypochlorite donor/bromide ion donor compositions are actually performing as a bromine biocide, a mixture of bromine and chlorine biocides, or as a chlorine biocide only. For example, consider the following four scenarios.

In the first scenario, the recirculating water does not contain any bromide ion. It follows then that there will be no hypobromite species present. Since the [Br$^-$]=0.0 and the [HOBr]=[OBr$^-$]=0.0, then hypochlorite species will have some finite values; e.g., 0.5 mole of HOCl and 0.5 mole of OCl$^-$. Also, CR=0.0 as shown by the following calculation:

$$CR = \frac{(0.0 + 0.0 + 0.0)}{(0.0 + 0.0 + 0.5 + 0.5)} = \frac{0.0}{1.0} = 0.0$$

Under these conditions, the biocide will perform as a chlorine biocide.

Assume in the second scenario that the recirculating water contains 0.5 mole of bromide ion, 0.5 mole of HOCl and 0.5 mole of OCl$^-$ before the hypochlorite species/bromide ion reactions occur. Under these conditions, there is only enough bromide ion to satisfy one-half of the stoichiometric requirements of the reactions outlined in equations 6a and 6b. Therefore, essentially all of the bromide ions will be converted to hypobromite species, but only one-half the hypochlorite species will be converted to hypobromite species. Also, one-half the hypochlorite species will still be present. Thus, the hypohalite species in the water will be a 50/50 mixture of hypochlorite species and hypobromite species and the CR will be 0.5 as shown by the following calculation:

[HOBr] + [OBr$^-$] = 0.5 mole
[HOCl] + [OCl$^-$] = 0.5 mole
[Br$^-$] = 0.0

$$CR = \frac{(0.5 + 0.0)}{(0.5 + 0.5)} = \frac{0.5}{1.0} = 0.5$$

Since the hypochlorite donor/bromide ion donor composition is capable of only maintaining a 0.5 Conversion Ratio, it will exhibit biocidal properties intermediate between that of a chlorine biocide and a bromine biocide. It follows then that any hypochlorite donor/bromide ion donor composition that maintains a Conversion Ratio between 0.0 and 1.0, will exhibit the same properties.

In the third scenario, assume that there are 1.0 mole of bromide ion and 1.0 mole of hypochlorite species (0.5 mole of HOCl and 0.5 mole OCl$^-$) before the HOCl/Br$^-$ and OCl$^-$/Br$^-$ reactions occur. Under these circumstances, essentially all of the hypochlorite species will be converted to hypobromite species. Similarly, essentially all of the bromide ions will be converted to hypobromite species. Hence, there will be essentially no hypochlorite species and bromide ions left. As a consequence, after the reactions, the Conversion Ratio will be 1.0 as shown by the following calculation:

[Br$^-$] = 0.0
[HOCl] = [OCl$^-$] = 0.0
[HOBr] + [OBr$^-$] = 1.0

$$CR = \frac{(1.0 + 0.0)}{(0.0 + 1.0)} = \frac{1.0}{1.0} = 1.0$$

And, the hypochlorite donor/bromide ion donor composition will perform as a bromide biocide.

Finally, in the fourth scenario, assume that the recirculating water contains 1.2 moles of bromide ion and 1.0 mole of hypochlorite species before the hypochlorite species react with the bromide ion. Upon completion of these instantaneous reactions, the recirculating water will contain essentially no hypochlorite species, 1.0 mole of hypobromite species and 0.2 mole of bromide ion. Accordingly, after the reactions, the Conversion Ratio will be 1.2 as shown below:

[HOCl] = [OCl$^-$] = 0.0
[HOBr] + [OBr$^-$] = 1.0
[Br$^-$] = 0.2
Thus, $$CR = \frac{(1.0 + 0.2)}{(1.0 + 0.0)} = \frac{1.2}{1.0} = 1.2$$

As a consequence, the hypochlorite donor/bromide ion donor composition will perform as a bromine biocide.

Thus, it is desirable to maintain the Conversion Ratio preferably at or slightly above 1.0. However, as will be shown later, there are circumstances where other Conversion Ratios are desirable. Hence, it is preferable to maintain the Conversion Ratio between about 0.2 and 20.0 and most preferably between 0.5 and 4.0.

In order to control the Conversion Ratio to maintain a small excess of bromide ion, enough bromide ion must be fed to the water to compensate for any significant losses of bromine containing species. Bromide ion is, of course, lost from recirculating water systems through blowdown or turnover. These terms refer to water that is bled from the system, a practice necessary to keep dissolved solids from building up to the point where scaling occurs. However, there has been no recognition in the literature that bromide ion is lost by volatilization of hypobromous acid and bromamines when combinations of hypochlorite donors and bromide ion donors are used to generate hypobromite species. Moreover, the literature contains no recognition that significant bromide ion losses can occur through the reaction of hypobromite species with organic materials in the recirculating water. Nor has the literature recognized the magnitude and the rate of bromide ion losses that can result from the volatilization and organobromine compound pathways. More importantly, the literature contains no recognition that knowledge of the bromide ion loss phenomenon may be used to develop compositions comprising hypochlorite donors and bromide ion donors that are capable of simultaneously compensating for the bromide ion losses and satisfying the chlorine demand of the recirculating water. Without knowledge of bromide ion loss pathways, as will be shown in the detailed description of this invention, it is virtually impossible to develop commercial products that will perform like bromine-based biocides without using a large excess of bromide ion. Thus, all significant pathways of bromide ion loss must be accounted for in order to maintain an optimum Conversion Ratio in the recirculating water.

The failure of the prior art to adequately compensate for bromide ion loss is evident in the prior art's use of either large excesses of bromide ion or of insufficient amounts to maintain maximum biocidal activity. Any large excess of bromide ion is wasted since it is eventually discarded, for example, in the cooling tower blowdown or pool water turnover. Also, as will be shown in the detailed description of the present invention, a large excess of bromide ion is unnecessary because the physical and chemical dynamics of the recirculating water system will force the bromide ion concentration to a steady state condition. In many cases, this will result in considerable loss of bromide ion. As a consequence, it is preferable and more economical to supply only sufficient bromide ion to the recirculating water to maintain the Conversion Ratio at, or slightly above, 1.0 to ensure maximum biocidal effectiveness.

In one aspect, the present invention provides a biocide composition containing a hypochlorite donor and a bromide ion donor in amounts sufficient to satisfy the chlorine demand of the system and maintain an optimum Conversion Ratio.

In another aspect, the present invention provides a method of treating recirculating water which comprises the steps of ascertaining the rates of bromide ion loss from the system due to blowdown, volatilization, and formation of stable organobromine compounds and adding a hypochlorite donor and a bromide ion donor in amounts sufficient to compensate for the bromide ion losses and maintain an optimum Conversion Ratio.

Suitable hypochlorite donors include gaseous chlorine, alkali metal and alkaline earth metal hypochlorites, chlorinated hydantoins, chlorinated oxazolidinones, chlorinated imidazolidinones, and chlorinated isocyanuric acid derivatives.

Suitable bromide ion donors include liquid bromine, bromine chloride, alkali metal and alkaline earth metal bromides, quaternary ammonium bromides, bromamines, brominated hydantoins, brominated sulfonamides, brominated succinimides, brominated oxazolidinones, brominated imidazolidinones, brominated isocyanurates, and salts of trihalide or mixed trihalide ions containing bromine.

In a preferred embodiment the hypochlorite donor and bromide ion donor are dry solids having a higher dissolution rate and a higher water solubility than hydantoins. Preferred dry solids include trichloroisocyanuric acid or sodium or potassium dichloroisocyanurate and sodium or potassium bromide. When these compounds are used, it has been found that proportions of about 85 to about 99 parts by weight hypochlorite donor and about 1 to about 15 parts by weight bromide ion donor are capable of maintaining the Conversion Ratio in the optimum range for most water systems. In other instances, e.g. when hydantoin derivatives are used as the bromide ion donor, different proportions are sometimes necessary. For these compounds, it has been found that proportions of about 50 to about 99 parts by weight hypochlorite donor and about 1 to about 50 parts by weight bromide ion donor are capable of maintaining an optimum Conversion Ratio.

It has now also been found that certain compounds can be added to the recirculating water system to suppress the loss of bromide ions through volatilization of hypobromous acid and bromamine. The bromine volatilization suppressants may be included in the hypochlorite donor/bromide ion donor biocide composition or combination thereof or may be added separately to the recirculating water. Suitable bromine volatilization suppressants include hydantoin derivatives, sulfonamide derivatives, sulfamic acid derivatives, glycoluril derivatives, oxazolidinone derivatives, imidazolidinone derivatives and succinimide derivatives.

Other features and advantages of the present invention will become apparent from the following detailed description, which is given by way of illustration only.

DETAILED DESCRIPTION OF THE INVENTION

Figure 1:
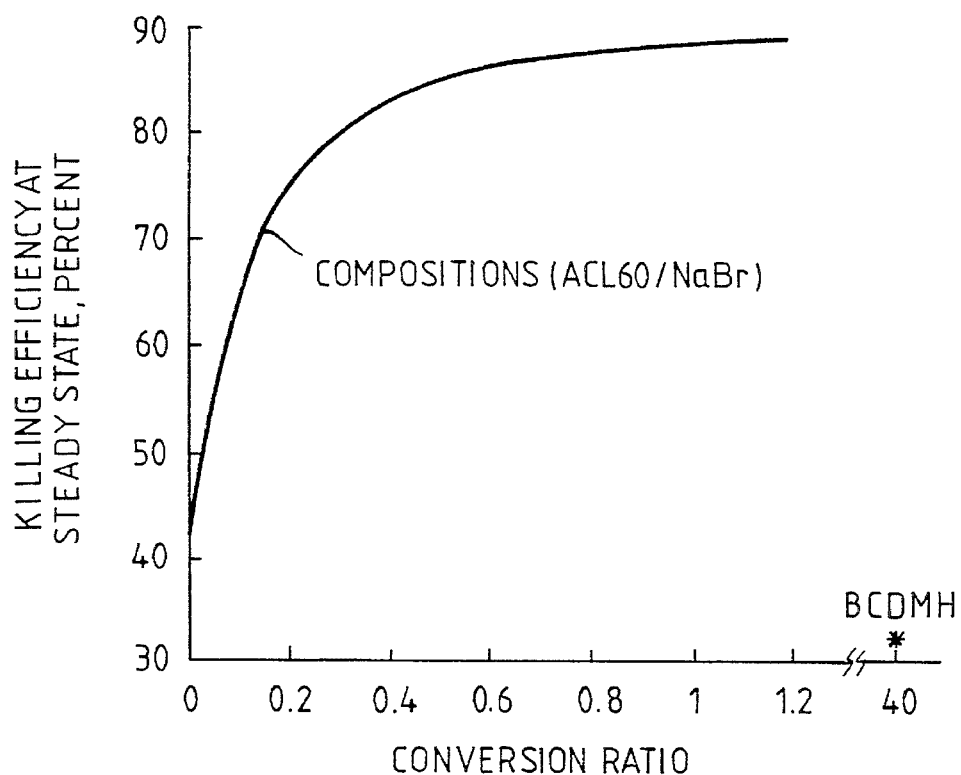
FIG. 1 illustrates the effect of the Conversion Ratio on killing efficiency.

A hypochlorite donor compound according to the present invention may be any chlorine containing compound capable of providing a sufficient amount of hypochlorite species in aqueous solution, including but not limited to gaseous chlorine, hypochlorite salts such as lithium hypochlorite, sodium hypochlorite, or calcium hypochlorite, chlorinated hydantoins such as dichlorodimethylhydantoin, or bromochlorodimethylhydantoin, chlorinated oxazolidinones such as 3-chloro-4,4-dimethyl-2-oxazolidinone, chlorinated imidazolidinones such as 1,3-dichloro-4,4,5,5-tetramethyl-2-imidazolidinone, or chlorinated isocyanuric acid or its derivatives including its salts, hydrates, complexes, or mixtures thereof.

Some disadvantages may occur with the use of certain of these hypochlorite donor compounds. For example, addition of calcium is not desirable since repeated use could increase the calcium ion concentration in the water to the level where calcium scaling problems could occur. Since chlorine gas is a hazardous material, its use is generally limited to the larger, more sophisticated recirculating water systems. Finally, many of the chlorinated organic compounds are less useful than the chlorinated isocyanuric acid derivatives due to higher costs, lower dissolution rates, lower halogen content, and/or the buildup of species which inhibit biocidal activity.

Preferred hypochlorite donor compounds include chlorinated isocyanuric acid derivatives chosen from the following group of compounds: sodium dichloro-s-triazinetrione (also called sodium dichloroisocyanurate, available from Monsanto Co. under the tradename ACL60), potassium dichloro-s-triazinetrione (available from Monsanto Co. under the tradename ACL59), the hydrate of sodium dichloro-s-triazinetrione (available from Monsanto Co. under the tradename ACL56), dichloroisocyanuric acid, trichloro-s-triazinetrione (also called trichloroisocyanuric acid, available from Monsanto under the tradename ACL90 PLUS), mixtures thereof such as [mono(trichloro)-tetra(monopotassium dichloro)]-penta-s-triazinetrione and [mono(trichloro)-mono(monopotassium dichloro)]-di-s-triazinetrione. These compounds are disclosed, for example, in U.S. Pat. Nos. 3,035,056; 3,035,057; 3,150,132; 3,256,199; 3,294,797; and 3,564,146.

The bromide ion donor according to the present invention may be any compound capable of providing a sufficient amount of bromide ion in aqueous solution including, but not limited to, liquid bromine, bromine chloride, alkali metal bromides, alkaline earth metal bromides, $R_4$-ammonium bromide where R is an alkyl or aryl group, bromamines, N-brominated organic compounds, such as N-brominated hydantoins, N-brominated sulfonamides, N-brominated oxazolidinones, N-brominated imidazolidinones, N-brominated imides such as N-bromosuccinimide or N-brominated isocyanurates which can release hypobromite species or salts of trihalide or mixed trihalide ions such as $Br_3^-$ or $ClBr_2^-$ as described in U.S. Pat. No. 3,152,073.

The hypochlorite donor compound and the bromide ion donor compound may be added either separately or as a single composition. For some combinations, the two components must be added separately, for example, chlorine gas and sodium bromide. In many cases, however, it is advantageous to premix the two components and add the compositions to the recirculating water system. This reduces the number of materials to be handled and thus the number of controls required. Thus, it is possible to introduce the biocide of the present invention into the recirculating water system by any of the following means: an erosion feeder, a floater, porous bags, perforated buckets or by hand dosing.

A preferred product is a solid dry mixture of a chlorinated isocyanuric acid derivative and a bromide ion donor, most preferably compacted in the form of a tablet, stick or puck. One or more compacting aids such as boric acid, sodium stearate, potassium stearate, aluminum hydroxide or monoglycerol stearate may optionally be used. To eliminate any possible interaction between the two components of the mixture it is necessary to eliminate any free water, as taught in U.S. Pat. No. 2,815,311. If free water is present, the two components may react to form bromine gas, which can corrode metallic containers or pose a health hazard to persons handling the material. In addition to optional compacting aids, the biocide of the present invention may also optionally include one or more scale inhibitor compounds such as polymaleic acid, polyacrylic acid, a phosphonate, a polyphosphate, or mixtures thereof.

When the product used is a mixture of a solid hypochlorite donor and a bromide ion donor, the appropriate composition depends on the operating characteristics of the individual recirculating water system. Therefore a range of compositions is required since there are a number of differences between systems. These differences include variation in the quality of the water used for makeup, variation in local air quality, variation in the blowdown or turnover rate, and other system variables. For a composition of trichloroisocyanuric acid and sodium bromide, the weight percent of sodium bromide in the composition required to provide the optimum Conversion Ratio in the recirculating water typically ranges from about 3% NaBr to about 15% NaBr, depending on how the recirculating water system is operated.

To maintain the Conversion Ratio in solution at the desired optimum, it is necessary to control both the sum of the concentrations of the hypohalite species (HOCl, OCl⁻, HOBr, and OBr⁻) and the sum of the concentrations of all bromine containing species (HOBr, OBr⁻, and Br⁻).

Control of the free halogen concentration is straightforward and is normally achieved for most systems, either with automated analyzer/control equipment or manually with the use of analytical test kits. Test kits and analytical control equipment determine free halogen concentrations by measuring the oxidizing potential of the species dissolved in the water. However, these devices are incapable of distinguishing whether the oxidizing potential was due to hypochlorite or hypobromite species. Consequently, the free halogen concentrations measured in the recirculating water systems are the sum of the free chlorine and the free bromine, and will usually be expressed in terms of free chlorine, since chlorine test kits are more widely used. The free halogen concentrations may also be expressed in terms of free bromine by: (1) multiplying the free chlorine reading by 2.25, which is the ratio of the molecular weights of molecular bromine to molecular chlorine (160/71=2.25) or (2) using a bromine test kit. However, when the Conversion Ratio in the recirculating water is one or greater, all of the free halogen species will be present as free bromine species, even though the free bromine may be expressed in terms of free chlorine.

Initially, it was believed that bromide ion would be a conserved specie in recirculating water systems, that is, that blowdown or turnover would be the only significant pathway for bromide ion loss. Blowdown or turnover loss, BrL(BD), may be calculated using the following equation, assuming constant bromide ion concentration:

$$BrL(BD) = Q_b \times C_{Br} \times \frac{3.79}{1000} \quad (9)$$

where:
BrL(BD)=bromide ion loss due to blowdown, gm/day
$Q_b$=blowdown or turnover rate, gal/day
$C_{Br}$=total concentration of all bromine species, mg/liter
3.79=conversion factor, gallons to liters
1000=conversion factor, grams to milligrams
Example: a system contains 1.0 mg Br/liter distributed between bromide ion and hypobromite species, and has a blowdown rate of 1000 gal/day. The calculated bromide ion loss due to blowdown would then be 3.79 gm Br/day.

Measurement of the bromide ion concentration during initial experiments has unexpectedly revealed the existence of other significant pathways of bromide ion loss. Further investigation has now demonstrated that in order to maintain an optimum Conversion Ratio, it is necessary to compensate for bromide ion losses by three additional pathways: 1) volatilization of hypobromous acid, 2) volatilization of bromamines and 3) formation of organobromine compounds. Loss of bromide ion by the volatilization of hypobromous acid occurs as a result of the reaction described in equation (6a).

Bromide ion losses via volatilization of bromamines occurs as a consequence of the reaction between hypobromous acid and nitrogenous contaminants (expressed in terms of ammonia).

$$HOBr + NH_3 \rightarrow BrNH_2 + H_2O \quad (10)$$

Organobromine compound formation occurs due to the reaction of hypobromous acid with organic matter in the water to form compounds with carbon-bromine bonds, for example:

$$HOBr + R-CH_3 \rightarrow R-CH_2Br + H_2O \quad (11)$$

The organobromine compounds include the trihalomethanes or other brominated alkanes, brominated carboxylic acids, and the like. The carbon-bromine bonds are very stable and not readily hydrolyzed. Hence, the bromine specie is no longer available as bromide ion for regeneration to hypobromous acid by hypochlorous acid. Therefore, the bromide ion has been effectively removed from this chemical recycle loop.

It is necessary to establish the magnitude of the bromide ion losses by these pathways in order to determine the appropriate proportions of bromide ion donor and hypochlorite donor to feed to the recirculating water system. This can be accomplished by two methods: 1) analytical determination of the decrease in bromide ion concentration ("the bromide ion analytical method") and 2) calculation of losses by the different pathways.

The determination of the appropriate amounts of bromide ion donor and hypochlorite donor can be achieved by the bromide ion analytical method as outlined in the following:

1. Take samples of the recirculating water at regular intervals and note the sample times.

2. Determine the bromide ion concentration of the water samples with ASTM D-1246-82a, Method D—Ion Selective Electrode For Bromide. Note, in this case, the hypohalite species (HOBr, $OBr^-$, HOCl, $OCl^-$) must be converted to halide species ($Cl^-$ and $Br^-$) prior to the determination of bromide ion. This is achieved by adding sodium sulfite to the solutions in amounts of 1.25 times the stoichiometric amount required to satisfy the following equation:

$$OX^- + Na_2SO_3 \rightarrow Na_2SO_4 + X^- \quad (12)$$

where:
$OX^- = OCl^-$ or $OBr^-$
$X^- = Cl^-$ or $Br^-$

3. Calculate the total daily loss of bromide ion TBrL, in grams per day by using the analytical and sample time data.

4. Determine the amount of bromide ion donor, BrD, required to compensate for the losses and maintain the bromide ion concentration at the desired level with the following equation:

$$BrD = \frac{M_{BrD}}{M_{Br}} \times TBrL \quad (13)$$

where:
BrD=amount of bromide ion donor required to compensate for losses and maintain the bromide ion concentration at the desired level, gm/day
$M_{BrD}$=mole weight of bromide ion donor, gm
$M_{Br}$=mole weight of bromide ion, gm
TBrL=total daily bromide ion losses, gm/day 5. Determine the daily chlorine demand, CD, of the system.

6. Determine the amount of hypochlorite donor compound required to satisfy the daily chlorine demand with the following equation:

$$HCD = \frac{CD}{AvC} \times 100\% \quad (14)$$

where:
HCD=amount of hypochlorite donor compound required to satisfy the chlorine demand, gm/day
CD=chlorine demand of the system, gm $Cl_2$/day
AvC=available chlorine content of chlorine donor (wt %)

7. For hypochlorite donor/bromide ion donor combinations where it is more practical to feed the two donors separately, the results of steps 4 and 6 indicate what the feed rates must be for the corresponding donors in order to satisfy the chlorine demand and bromide ion donor requirements and to make the combinations perform as bromine biocides.

8. For a hypochlorite donor/bromide ion donor combination that will be contained in a single composition or product, a composition is determined by the following calculations:

Hypochlorite Donor/Bromide Ion Donor Composition Requirements $$BGC = HCD + BrD \quad (15)$$

where:

BGC=amount of hypochlorite donor/bromide ion donor composition required to satisfy the chlorine demand and bromide ion requirements simultaneously, gm/day b. Hypochlorite Donor/Bromide Ion Donor Composition $$\% \text{ hypochlorite donor} = \frac{HCD}{BGC} \times 100\% \quad (16)$$

$$\% \text{ bromide ion donor} = \frac{BrD}{BGC} \times 100\% \quad (17)$$

Although it is an alternative to calculating the appropriate amounts of bromide ion donor and hypochlorite donor to feed to the system, the bromide ion analytical approach is generally beyond the sophistication of most cooling tower, swimming pool and spa operations or would require a considerable expense for added instrumentation.

The present invention obviates the need for this costly instrumentation, since the appropriate amounts of hypochlorite donor and bromide ion donor may also be established by the second method, that is, by calculating bromide ion losses. Investigations relating to the present invention demonstrate that the bromide ion can be lost by pathways other than blowdown. At the optimum Conversion Ratio, the losses incurred by these pathways can be several times larger than the blowdown loss, making it virtually impossible to maintain the desired Conversion Ratio without knowledge of these pathways. The magnitudes of the losses by the various pathways are totally surprising. At Conversion Ratios much higher than optimum, the percentage of the total bromide ion lost by these pathways is much lower, because the ionic bromide form is not volatile. In such cases, the volatilization losses are not readily apparent. Thus, since prior art use of bromide-based biocides was not at the optimum Conversion Ratio, the loss of bromide ion by these pathways was not recognized. Because bromide ion was usually present in excess, the prior art did not perceive the importance of these additional bromide ion loss pathways.

The amount of bromide ion lost by flashoff of HOBr, BrL(FL), may be calculated using either equation (18) or (19).

$$BrL(FL) = \frac{f \times H_k}{W_L/W_G} \times R \times C_{HOBr} \times \frac{M_W}{M_a} \times \frac{M_{Br}}{M_{HOBr}} \times \frac{3.79}{1000} \quad (18)$$

or $$BrL(FL) = fH_kQ_aD_aC_{HOBr} \times \frac{M_W}{M_a} \times \frac{M_{Br}}{M_{HOBr}} \times \frac{28.316}{1000} \times 1440 \quad (19)$$

where:
BrL(FL)=amount of bromide ion lost by flashoff of hypobromous acid, gm Br/day
R=the recirculation rate of the recirculating water system, gal/day
f=flashoff equilibrium coefficient for the recirculating water system. (Note, f has a value between 0 and 1.)
$H_k$=Henry's Law Constant for hypobromous acid at the pH and temperature of the recirculating water system
$Q_a$=the flow rate of air through the tower, $ft^3$/min.
$D_a$=density of air, gm/L
$W_L/W_G$=ratio of the mass flow rate of the recirculating water to the mass flow rate of air through the system
$M_{HOBr}$=mole weight of hypobromous acid, gm
$C_{HOBr}$=the concentration of hypobromite species as hypobromous acid, mg HOBr/L
$M_W$=mole weight of water, gm
$M_a$=mole weight of air, gm
$M_{Br}$=mole weight of bromide ion, gm 3.79=conversion factor, gallons to liters
1000=conversion factor, grams to milligrams
28.316=conversion factor, cubic feet to liters
1440=conversion factor, days to minutes It is important to point out that the value of $C_{HOBr}$, the concentration of hypobromite species, is not the same as $C_{Br}$, the sum of concentrations of all bromine-containing species, since some of the bromine species present can be in the form of bromide ion.

Henry's Law constant is defined by the following equation:

$$H_k = \frac{C_{solute\ (gas)}}{C_{solute\ (liquid)}} \quad (20)$$

where:
$H_k$=Henry's Law Constant
$C_{solute\ (gas)}$=concentration of volatile solute in the gas phase
$C_{solute\ (liquid)}$=concentration of volatile solute in the liquid phase Henry's Law constant is, therefore, the ratio of the concentration of solute in the vapor phase at equilibrium to the concentration of the solute dissolved in a solvent, in these cases water. This constant is a measure of the tendency of the dissolved solute to escape or volatilize from the solvent. A low Henry's Law constant indicates little tendency for the solute to volatilize. A high constant value indicates a greater tendency of the solute to escape from the solution into the gas phase. Henry's Law constants can be expressed in any combination of a number of concentration units, such as partial pressure, milligrams per liter, or mole fraction. Herein, mole fraction units are used for both the gas and liquid phase concentrations.

As an example, a cooling tower has $W_L/W_G$=1.3, f=0.5, R=400,000 gallons/day, and the tower operates at pH=8.0 and 30° C. For the conditions in this particular example, Henry's Law constant is 0.25. The concentration of free halogen is 0.5 mg/L (0.5 ppm, free chlorine basis). The bromide ion concentration is maintained at 0.8 mg/L (0.8 ppm) to give a Conversion Ratio of 1.05, slightly greater than the optimum value of 1. Thus, all of the free halogen species are essentially free bromine species (HOBr and OBr⁻). As a result, the free bromine concentration in terms of hypobromous acid is 0.685 mg/L [$C_{HOBr}$=FAvC×$M_{HOBr}$/$M_{Cl_2}$0.5×96.9/71=0.685]. Under these conditions, the flashoff loss of bromide ion via the volatilization of hypobromous acid is 51.1 grams of bromide ion per day. This loss is considerably larger than that due to blowdown (cf. blowdown loss calculation above), demonstrating that volatilization of hypobromous acid can be a major factor contributing to the loss of bromide ion from recirculating water systems.

The Henry's Law constant for hypobromous acid used in the above example was determined as follows, using a pilot scale cooling tower since there is no literature data for hypobromous acid or any of the bromamines. The pilot cooling tower was a counterflow type with a capacity of 80 liters of water, which was circulated through the tower at 1.2 gal/min. The air flow rate was 2800 L/min. An electrical heater, placed in the recirculation line, provided a constant heat source. In each experiment, the pilot tower was filled with chlorine-demand-free water and an appropriate amount of biocide was added to give 4.0 mg/L (as chlorine). During the test, the biocide concentration was continuously monitored using a Hach CL17 chlorine analyzer. The water was initially recirculated with no air flow for 30 minutes to establish a baseline free halogen concentration. The air flow was then started and the free halogen concentration was monitored for four hours. The drop in the halogen concentration during this period, which is due to volatilization of any volatile species, can be used to calculate the Henry's Law constant using the following equation:

$$H_k = -\frac{(\log C_f - \log C_i)}{t} \times \frac{2.303\ V_w D_w M_a}{Q_a D_a M_w}$$

where:
$H_k$=Henry's Law constant at temperature and pH of the experiment
$V_w$=volume of recirculating water, liters
$D_w$=density of water, gm/ml
$D_a$=density of air, gm/ml
$M_w$=mole weight of water, gm
$M_a$=mole weight of air, gm
$Q_a$=volumetric air flow, L/min
$C_f$=final halogen concentration, mg/L
$C_i$=initial halogen concentration, mg/L
t=length of time of experiment, min This procedure assumes that the hypobromous acid has reached equilibrium between the gas and liquid phases. With this method, Henry's Law constants were determined for hypobromous acid as a function of pH, temperature, and the concentration of additional chemical species.

As stated previously, the presence of ammonia in the recirculating water has also been found to increase the loss of bromide ion. This is due to the formation of various bromamine compounds, especially monobromamine, which is more volatile than hypobromous acid. The effect of ammonia on the volatility of hypobromous acid is reflected in an increase in the Henry's Law constant. This change in the Henry's Law constant is dependent on the ratio of ammonia to free bromine, the pH, and the temperature. There are no literature values for the Henry's Law constants for bromamines. The results of our measurements indicate the Henry's Law constant for bromamines is considerably larger than the Henry's Law constant for hypobromous acid under the same conditions. The simple bromamines are, therefore, very volatile and do not build up to significant levels because they are flashed off very rapidly.

Under steady state conditions, the loss of the simple bromamines by flashoff will be approximately equal to the rate of formation of monobromamine. The bromamine formation rate is determined by the rate of introduction of ammonia into the recirculating water. In most cases, the major source of ammonia is the makeup water. Thus, the flashoff loss due to formation of bromamines, BrL(BA), can simply be estimated by the following equation:

$$\text{BrL(BA)} = C_{NH_3} \times Q_m \times \frac{M_{Br}}{M_{NH_3}} \times \frac{3.79}{1000} \quad (21)$$

where:
BrL(BA)=amount of bromide ion lost by flashoff of bromamines, gm/day
$C_{NH_3}$=concentration of ammonia in makeup water, mg/L
$Q_m$=makeup water rate, gal/day
$M_{Br}$=mole weight of bromide ion, gm
$M_{NH_3}$=mole weight of ammonia, gm
3.79=conversion factor, gallons to liters
1000=conversion factor, grams to milligrams
Note, equation (21) applies only to relatively small ammonia concentrations.

Another significant pathway for bromide ion loss is the formation of organobromine compounds as a result of the reaction of hypobromous acid with organic molecules dissolved or suspended in the water. Carbon-bromine covalent bonds are usually stable to hydrolysis so that the bromine is not released back into the water and is not available for regeneration to hypobromite species. The amount of bromide ion loss can vary widely depending on the organic content of the water, which can be quantified as TOC. TOC, or total organic carbon (in mg/L), measures the total amount of organic material dissolved or suspended in the water, without distinguishing the chemical form. Several commercial analyzers are available which perform this analysis. Lab experiments with both tap water and untreated surface water have shown that about 0.2 mg/L of bromide ion is combined as organobromine compounds for every mg/L of TOC introduced into the water. This number varies somewhat depending on the individual water source, but 0.2 is a reasonable estimate for most cases.

The amount of bromide ion loss caused by the formation of organobromine compounds, BrL(OBr) can be calculated with the following equation, which accounts for the total organic carbon introduced with the makeup water:

$$\text{BrL(OBr)} = Q_m \times 0.2 \times TOC \times \frac{3.79}{1000} \qquad (22)$$

where:
BrL(OBr)=amount of bromide ion lost due to the formation of organobromine compounds, gm/day
$Q_m$=makeup water rate, gal/day
TOC=total organic content of makeup water, mg/L
0.2=amount of bromide ion lost per mg/L of TOC in recirculating water, mg/L
3.79=conversion factor, gallons to liters
1000=conversion factor, grams to milligrams Note, equation (22) applies only to relatively small TOC concentrations. This calculation does not account for any TOC added from sources other than makeup, for instance, organic or biological contamination absorbed from the air blown through the tower or contamination from process leaks. If such contamination is severe, the additional loss of bromide ion by reaction with these sources of TOC should also be accounted for.

It is necessary to quantify the major pathways of bromide ion loss, blowdown, flashoff, and organobromine formation in order to determine the appropriate proportions of bromide ion donor and hypochlorite donor to feed to the recirculating water system. Once each of the bromide ion pathway losses are quantified, the optimum proportions of bromide ion donor and hypochlorite donor to be fed to the system may be calculated according to the following steps:

1) Define the desired free halogen concentration (available chlorine basis), FAvC, and the desired Conversion Ratio, CR. CR may range from about 0.2 to about 20.0, more preferably from about 0.2 to about 10.0, and most preferably from about 0.5 to about 4.0. If excess bromide ion is desired CR should be greater than 1.0; if not, then CR can be less than 1.0.

2) Convert the desired free halogen concentration to the concentration of hypobromous acid, $C_{HOBr}$, by multiplying the free chlorine concentration, FAvC, by 1.37×CR if CR is less than 1.0 or by 1.37 if CR is greater than 1.0. The factor 1.37 is equal to 96.916/70.906 (molecular weight of HOBr/ molecular weight of chlorine).

3) Calculate the desired total concentration of all bromine containing species, $C_{Br}$, in terms of bromide ion, using the following equation:

$$C_{Br} = FAvC \times CR + \frac{M_{Br}}{M_{Cl_2}}$$

4) Calculate the daily bromide ion loss caused by blowdown, BrL(BD), with equation (9).

5) Calculate the daily bromide ion loss incurred by the flashoff of hypobromous acid, BrL(FL), using either equation (18) or (19).

6) Calculate the daily bromide ion loss caused by bromamine flashoff, BrL(BA), with equation (21).

7) Calculate the daily bromide ion loss caused by the formation of organobromine compounds, BrL(OBr), using equation (22).

8) Calculate the total daily bromide ion loss, TBrL, by combining the results of the calculations in steps 4, 5, 6, and 7.

$$TBrL = BrL(BD) + BrL(FL) + BrL(BA) + BrL(OBr) \qquad (23)$$

9) Determine the daily quantity of bromide ion donor required to compensate for bromide ion losses with equation (13).

10) Determine the amount of hypochlorite donor required to satisfy the daily chlorine demand with equation (14).

11) For hypochlorite donor/bromide ion donor combinations where it is more practical to feed the two donors separately, the results of steps 9 and 10 indicate what the feed rates must be for the corresponding donors in order to satisfy the chlorine demand and bromide donor requirements simultaneously and make the combination perform as a bromine biocide.

12) For products containing both the hypochlorite donor and bromide ion donor as a single composition or mixture, determine the appropriate composition with equations (15), (16) and (17).

The effectiveness of the hypochlorite donor/bromide ion donor biocides and the bromine volatilization suppressants disclosed herein is demonstrated in the following examples, including killing efficiency experiments, cooling tower and spa tests, and calculations in which compositions representative of the present invention, such as ACL60/NaBr and ACL90 PLUS/NaBr, are compared with chlorine (ACL60) and competitive bromine (BCDMH) biocides.

EXAMPLE 1

Effectiveness of Hypochlorite Donor/Bromide Ion Donor Compositions In Cooling Towers A small crossflow, induced draft cooling tower, used to cool a 250 ton air conditioning system, was used to test the relative effectiveness of the current invention versus chlorine and BCDMH biocides over a period of five months. The pH of the tower water was controlled at 8.5 and the free halogen concentration was controlled at 0.5 mg/L (available chlorine base) with an automated chlorine analyzer/controller. Scale and corrosion inhibitors were also added as part of the normal operation of the cooling tower. The effectiveness of each biocide was judged on the ability of the biocide to control the biofouling microorganism population as measured by a standard plate count method. Microorganism populations were reported as colony forming units per milliliter (CFU/ml). Samples for the determination of microorganism populations and bromide ion concentration were taken from the same location in the cooling tower basin away from the point of chemical addition. Two to three samples were taken per day. Immediately after sampling, any hypohalite species were reduced to halide species with sodium thiosulfate. The bromide ion concentration was measured by ion chromatography. The results of the test are shown below in Table 1:

TABLE 1

Results of Cooling Tower Biofouling Control Tests Comparing Biocidal Effectiveness of Hypochlorite Donor/Bromide Ion Donor Biocide Compositions to Chlorine and Bromine Biocides.

| Biocide Tested | Total Br Conc (mg/L) | Plate Count (CFU/ml) | Conversion Ratio |
|---|---|---|---|
| ACL60 | 0.0 | 14,200 | 0.0 |
| ACL60/NaBr | 0.14 | 5,600 | 0.25 |
| ACL90 PLUS/NaBr | 1.8 | 4,200 | 3.2 |
| BCDMH | 23.2 | 24,600 | 41.1 |
| ACL60/NaBr | 18. | 1,600 | 31.9 |
| ACL90 PLUS/NaBr | 6.5 | 1,200 | 11.5 |

Notes:
1. Results are the average values observed during the test periods. 2. Test Conditions: pH = 8.5; free halogen = 0.5 mg/L, available chlorine basis.

In these tests, ACL60 (sodium dichloroisocyanurate) was used to demonstrate the biocidal effectiveness of chlorine biocides under these conditions. Combinations of sodium bromide with ACL60 and sodium bromide with ACL90 PLUS (trichloroisocyanurate) were employed to illustrate the effect of the Conversion Ratio on the biocidal effectiveness of the hypochlorite donor/bromide ion donor compositions, which are representative of the present invention, and their ability to perform as bromine biocides. BCDMH was also included to compare the effectiveness of this bromine biocide to the ones representative of the present invention.

The results of these tests show that the hypochlorite donor/bromide ion donor compositions of NaBr/ACL60 and ACL90 PLUS/NaBr, were not only superior to the chlorine biocide, ACL60, but were also superior to the bromine biocide, BCDMH, in controlling the population of the biofouling microorganisms. The most effective NaBr/ACL60 and NaBr/ACL90 PLUS biocide compositions were those which maintained the Conversion Ratio in the recirculating water above 1.

The biocide compositions that were less effective were those which produced Conversion Ratios of less than one. However, all of the NaBr/ACL compositions were more effective than the chlorine (ACL60) and BCDMH biocides, as evidenced by the fact that they controlled the biofouling microorganism population at or below 6000 CFU/ml, whereas the chlorine and BCDMH biocides were not capable of reducing the biofouling populations below 14,000 and 24,000 CFU/ml, respectively, at the same free halogen concentration.

EXAMPLE 2

Effectiveness of Hypochlorite Donor/Bromide Ion Donor Biocide Compositions in Biofouling Control Experiments The killing efficiencies of the biocides evaluated in Example 1 were also determined in laboratory experiments designed to simulate cooling tower conditions. In these experiments, a culture of microorganisms from the cooling water in Example 1 were cultured in a well-stirred vessel by metering nutrient solution into the solution containing the culture. The vessel contents were maintained at 37° C. and pH of 8.0. Each experiment consisted of shocking the microorganisms with the biocide to be tested. Nutrient solution was also fed continuously to the vessel to encourage growth of the microorganisms and biocide solution was fed to the vessel to control the free halogen concentration at 0.5 mg/L (available chlorine basis) and the microorganism population. The microorganism population was determined periodically by an HMB-II apparatus (KVM Engineering) until the microorganism population had ceased to decline and remained constant for several hours. This usually occurred in about four hours after the start of the experiment. At this point, the microorganism growth rate and the microorganism death rate due to the biocidal activity of the biocide were considered to be in dynamic equilibrium, or at steady state. The effectiveness of biocide was then judged on the basis of killing efficiency as defined by the following expression.

$$KE = \frac{[P_i - P_f]}{P_i} \times 100\% \tag{24}$$

where:
KE=killing efficiency of the biocide, %
$P_i$=microorganism population at the start of the experiment, CFU/ml
$P_f$=microorganism population at steady state conditions, CFU/ml The results of the biocide killing efficiency experiments are summarized in Table 2.

TABLE 2

Results of Biocide Killing Efficiency Experiments

| Biocide Tested | NaBr/ ACL 60 Wt. Ratio | CR | $P_i$ (CFU/ml) | $P_f$ (CFU/ml) | KE |
|---|---|---|---|---|---|
| BCDMH | — | — | 2,140,000 | 1,260,000 | 41 |
| ACL60 | 0.0 | 0.0 | 1,560,000 | 880,000 | 44 |
| ACL60/NaBr | 0.1 | 0.13 | 1,960,000 | 830,000 | 58 |
| ACL60/NaBr | 0.19 | 0.22 | 1,410,000 | 350,000 | 75 |
| ACL60/NaBr | 1.0 | 1.20 | 1,460,000 | 165,000 | 89 |

Conditions: pH=8.5, temperature=37° C., free halogen= 0.5 mg/L (available chlorine basis).

The results in Table 2 show that the NaBr/ACL60 compositions (hypobromous acid generating compositions) have superior biocidal activity relative to the chlorine biocide, ACL60, and the bromine biocide, BCDMH, under the conditions of the experiments. The results also support the validity of the results obtained in the cooling tower tests (Example 1). The above results also show that the best killing efficiency was obtained at a Conversion Ratio of 1.20. This represents the condition where the amount of NaBr is sufficient to make the bromide ion concentration in the water slightly in excess of the stoichiometric amount required to satisfy the reactions shown in equations (6a) and (6b). Thus, the best killing efficiency was obtained with the composition that performed as a true bromine biocide. However, the results of the experiments indicate that the killing efficiencies of NaBr/ACL60 compositions which yield Conversion Ratios of less than 1 are still better than the chlorine (ACL60) or BCDMH biocides.

The effect of the Conversion Ratio can be understood more clearly by referring to the graph shown in FIG. 1. FIG. 1 is a plot of the killing efficiency of each ACL60/NaBr composition tested as a function of the Conversion Ratio. The results show that killing efficiencies increase as the Conversion Ratios increase until the maximum killing efficiency is attained near a Conversion Ratio of 1.0. At this point, all of the free halogen species are free bromine species. FIG. 1 also shows that most of the improvement in killing efficiency (from 42% to 75%) occurred between Conversion Ratios of 0.0 and 0.2. This indicates that the Conversion Ratio in the recirculating water system does not have to be controlled tightly in order for the bromine based biocide to be significantly better than chlorine biocides at pH levels of 8 or higher.

Even though the performance of the hypochlorite donor/bromide ion donor biocide will be very good at these low ratios, it is desirable to use these biocides at Conversion Ratios of 1.0 or more, because the biocides will control the microorganisms more effectively, thereby reducing biocide usage, and because the formation of chloramines will be minimized. FIG. 1 shows at what levels the Conversion Ratio should be maintained to obtain maximum biocidal activity. However, it would not be economical, in most instances, to use products with proportions of bromide ion donor and hypochlorite donor equivalent to the desired Conversion Ratio in the recirculating water. Therefore, it is important to understand how to develop compositions and methods that allow hypochlorite donor/bromide ion donor compositions with low bromide ion donor contents to maintain the desired Conversion Ratio in the recirculating water.

EXAMPLE 3

Discovery of Bromide Ion Loss Phenomenon

During tests run on the cooling tower system described in Example 1, ACL90 PLUS (trichloroisocyanurate) was fed to the recirculating water system at a rate sufficient to maintain a free halogen concentration of 0.5 mg/L (0.5 ppm, free chlorine basis). The chlorine demand of the recirculating water system was determined to be about 282 grams of available chlorine per day. Since ACL90 PLUS, which has an available chlorine content of 90.7%, was used as the hypochlorite donor, the ACL90 PLUS requirement was 310.4 grams/day [(282÷0.907)×100%]. Sodium bromide was fed to the system at a rate of 2.6 gm NaBr/day, a rate calculated to account for blowdown loss and maintain a bromide ion concentration of 0.56 mg/L, a concentration sufficient to maintain a Conversion Ratio of one. Analyses of water samples taken from the system revealed, however, that the bromide ion was consistently as low as about 0.05 mg/L, considerably below the desired bromide ion concentration of 0.56 mg/L. Therefore, the bromide ion was lost at a rate much higher than expected.

EXAMPLE 4

Demonstration of the Bromide Ion Loss Phenomenon

Tests were conducted in the following manner. The blowdown value for the recirculating water system of the cooling tower cited in Example 1 was closed to prevent the loss of water by this pathway. The recirculating water system was then dosed with enough sodium bromide to obtain a concentration of about 0.5 mg/L (0.5 ppm) of bromide ion. The free halogen was maintained at 0.5 mg/L (0.5 ppm, free chlorine basis). The water was then recirculated for about one hour to obtain a uniform concentration of bromide ion throughout the system. Water samples were then taken periodically over a 24 hour period and analyzed for bromide ion. The results of the analyses in Table 3 show that about 70% of the bromide ions were lost during this 24 hour period. Loss rates for the first few hours were actually even higher. For instance, the loss rate for the first 8.5 hours is over 6% per hour or 152% per day.

TABLE 3

| | | Bromide Loss Data for Zero Blowdown | | |
|---|---|---|---|---|
| Water Sample | Time (hr) | Bromide Ion Conc (ppm) | Bromide Ion Losses (%) | Lithium Conc (ppm) |
| 1 | 0.0 | 0.50 | 0.0 | 0.42 |
| 2 | 8.5 | 0.20 | 54.0 | 0.40 |
| 3 | 24.0 | 0.13 | 69.0 | 0.41 |

To prove that the bromide ion losses were not due to leaks in the recirculating water system, the water was also spiked with lithium chloride at the start of this test. Lithium is not commonly found in water, can be easily analyzed for, and is not volatilized from the water system. The water samples taken for bromide analyses were also analyzed for lithium. The results shown in Table 3 demonstrate that lithium was not lost from the system during the test, thereby demonstrating that the bromide ion losses were not due to leaks, but, instead were due to other phenomena.

This example also demonstrates that the bromide ion losses can be significant in recirculating water systems, a fact not recognized by the prior art. In addition, it shows that many of the compositions described in the prior art for mixtures of hypochlorite donors and bromide ion donors actually performed as chlorine biocides instead of performing as bromine biocides like the claimed compositions. Furthermore, the results clearly indicate that without the knowledge of these losses, it would be impossible to make hypochlorite donor/bromide ion donor compositions which would perform efficiently and economically as bromine biocides.

EXAMPLE 5

Compensation for Bromide Ion Loss

This example demonstrates that with knowledge of the existence of the bromide ion loss phenomena, bromide ion losses can be adequately compensated for to produce the desired results—performance of hypochlorite donor/bromide ion donor composition as bromine biocides. As shown in Example 3, prior to the discovery of the bromide ion loss phenomena, the sodium bromide was fed to the cooling water system at the rate of 2.6 grams/day, an amount only sufficient to maintain a Conversion Ratio of 0.1 (0.05 ppm divided by 0.5 ppm free chlorine), far below the ratio required to make the free halogen species perform as a bromine biocide.

The results in Examples 3 and 4 indicated that the estimated sodium bromide feed rate had to be considerably higher than the original rate (2.6 grams/day) in order to maintain a Conversion Ratio of approximately one. Tests showed that a sodium bromide feed rate of 15–17 grams/day maintained the desired bromide ion concentration. Furthermore, the biocidal system performed as bromine biocide as evidenced by the reduction in biofouling organism population from 14,000 CFU/ml for the 0.01 Conversion Ratio in Example 3 to 5000 CFU/ml.

23
EXAMPLE 6

Determination of Appropriate Hypochlorite Donor/Bromide Ion Donor Biocide Composition by the Bromide Ion Analytical Method The following is an example of how this method can be applied to the determination of the appropriate hypochlorite donor compound/bromide ion donor composition for this cooing tower system.

In Example 5, the bromide ion donor (sodium bromide) requirement was determined to be 15.0–17.0 gm/day in order to maintain the bromide ion concentration at the level necessary to make the biocide perform as a bromine biocide. The hypochlorite donor/bromine ion donor composition requirement, BGC, for this particular combination was 327.4 grams/day (310.4+17.0). Therefore, the appropriate composition was 94.8% ACL90 PLUS [(310.4÷327.4)× 100%)] and 5.2% [(17.0÷327.4)×100%] sodium bromide.

If it is desired to add these two donors as a single product, the ACL90 PLUS and sodium bromide may be blended together, compacted into tablets, placed in an appropriate erosion feeder, and used to satisfy the chlorine demand and bromide ion requirements of the system. The composition would perform in the above described system as a bromine biocide. If it is desired to add the ACL90 PLUS and sodium bromide separately, the feed rates would be 310.4 and 17.0 gm/day respectively.

EXAMPLE 7

Bromide Ion Loss and Composition Calculations for Cooling Towers

An example of the procedure outlined above for calculating the total bromide ion loss and the hypochlorite donor/ bromide ion donor composition required to maintain the optimum Conversion Ration is given below. Three cooling towers, having the characteristics given in Table 4A, will be used. The three towers are various sizes and have somewhat different operating characteristics. A major difference between the three towers is the quality of the makeup water, which has a significant impact on the amount of bromide ion loss.

TABLE 4A

| Characteristics of Model Cooling Towers | | | |
|---|---|---|---|
| Characteristic | Tower A | Tower B | Tower C |
| Blowdown Rate, $Q_b$ (gal/day) | 1,000 | 2,000 | 12,000 |
| Recirculation Rate, R (gal/day) | 200,000 | 600,000 | $1.5 \times 10^7$ |
| Makeup Rate, $Q_m$ (gal/day) | 5,000 | 10,000 | 63,000 |
| Desired Free Halogen Conc., FAvC (mg/L, as chlorine) | 0.3 | 0.2 | 0.1 |
| Desired Conversion Ratio, CR | 1.1 | 0.9 | 1.2 |
| Flashoff Equilibrium Coefficient, f | 0.5 | 0.5 | 0.5 |
| $W_L/W_G$ | 1.3 | 1.3 | 3.0 |
| Tower-Top Temperature (°C.) | 30 | 30 | 30 |
| pH | 8.0 | 8.0 | 8.0 |
| Ammonia Concentration in Makeup Water (mg $NH_3$/L) | 0.0 | 0.1 | 0.1 |
| TOC Concentration in Makeup Water (mg TOC/L) | 2.0 | 1.0 | 1.0 |
| Biocide Usage (grams ACL90 PLUS/day) | 400 | 700 | 3,300 |

From the characteristics in Table 4A, the following parameters can be found for the three example towers. Sodium bromide (mol. wt.=102.90 gm/mole) is used as the bromide ion donor and ACL90 PLUS is the hypochlorite donor.

TABLE 4B

| Calculated Parameters of Model Cooling Towers | | | |
|---|---|---|---|
| Calculated Parameter | Tower A | Tower B | Tower C |
| HOBr Concentration, $C_{HOBr}$ (mg/L) | 0.410 | 0.246 | 0.137 |
| Total Br Conc, $C_{Br}$ (mg/L) | 0.372 | 0.203 | 0.135 |
| Henry's Law Constant, $H_k$ | 0.250 | 0.250 | 0.250 |
| Blowdown Loss, BrL(BD), grams Br/day | 1.41 | 1.54 | 6.15 |
| HOBr Flashoff Loss, BrL(FL), grams Br/day | 15.30 | 27.54 | 165.75 |
| Bromamine Flashoff Loss, BrL(BA), grams Br/day | 0.0 | 17.78 | 112.01 |
| Organobromine Compound Formation Loss, BrL(OBr), grams Br/day | 7.58 | 7.58 | 47.75 |
| Total Bromide Ion Loss, TBrL, grams Br/day | 24.29 | 54.44 | 331.67 |
| Total NaBr Needed, grams/day | 31.28 | 70.10 | 427.09 |
| % NaBr Needed in ACL90 PLUS/NaBr Composition | 7.25 | 9.10 | 11.46 |

The above calculations show that the flashoff losses can be much larger than the blowdown loss, especially when ammonia is present. Given the values above, the appropriate composition of a trichloroisocyanuric acid/NaBr mixture is calculated to be 7.25% NaBr for Tower A, 9.10% NaBr for Tower B and 11.46% NaBr for Tower C. If the flashoff losses and the loss due to formation of organobromine species are not accounted for, the appropriate composition would mistakenly be calculated as only 0.35% NaBr for Tower A, 0.22% NaBr for Tower B and 0.19% for Tower C.

If chlorine gas is being used as the hypochlorite donor, then the second to last line in Table 4B gives the amount of sodium bromide that must be added separately to maintain the optimum Conversion Ratio in the recirculating water.

EXAMPLE 8

Determination of an Appropriate Hypochlorite Donor/Bromide Ion Donor Biocide Composition This example demonstrates why understanding of bromide ion loss phenomena is critical to development of commercial biocides containing both hypochlorite donors and bromide ion donors.

In this example, a cooling tower system with a recirculating water capacity of 100,000 gallons is treated with ACL90 PLUS to maintain a free available chlorine concentration of 0.5 mg/L (0.5 ppm) in the water. The daily available chlorine demand is satisfied with 11.0 pounds of ACL90 PLUS. Since the available chlorine content of ACL90 PLUS is 90.7%, 11.0 pounds of ACL90 PLUS tablets per day are equivalent to 10.0 pounds of available chlorine (11.0×0.907=10.0).

The ACL90 PLUS chlorine biocide can be made to perform as a bromine biocide by adding sufficient sodium bromide to the water to maintain a Conversion Ratio of at least 1.0. This requires maintenance of a bromide ion concentration in the cooling water sufficient to satisfy the stoichiometric requirements of equations (6a) and (6b). Hence, the bromide ion concentration must be 0.56 ppm (0.5 ppm of $Cl_2 \times M_{Br}/M_{Cl_2}$=0.5×79.909/70.906=0.56). Since the recirculating water in the example cooling tower weighs 834,000 pounds (100,000 gallons×8.34 pounds/gallon), it must contain at least 0.47 pounds of bromide ion (0.56×10⁻

6×834,000 pounds=0.47 pounds). This requires that the water contain a minimum of 0.605 pound of sodium bromide (0.47 pound×$M_{NaBr}/M_{Br}$=0.47×102.90/79.909=0.605).

To make an ACL90 PLUS/NaBr composition perform as a bromine biocide, the composition must contain sufficient sodium bromide to build the bromide ion concentration up to and maintain it at the level required to satisfy the optimum Conversion Ratio. This can be achieved by knowing the bromide ion loss rates for the recirculating water system. If the ACL90 PLUS/NaBr product contains the exact amount of sodium bromide to compensate for the losses and maintain the Conversion Ratio at exactly one, then the sodium bromide concentration will automatically change with time until the desired concentration is reached. This occurs as follows:

When feeding a NaBr/ACL composition to a tower which initially contains no bromide ion, the bromide ion concentration will increase. The bromide ion loss rate depends on the concentration, so that the loss rate at low concentrations is very small, but slowly increases as the concentration of bromide ion increases. Thus, the initial bromide ion addition rate is larger than the bromide ion loss rate and the bromide ion concentration increases. This continues until the bromide ion loss rate matches the rate at which bromide ion is added to the system. At this point, a dynamic equilibrium condition, commonly referred to as a steady state, has been reached. Under these conditions, the bromide ion loss rate is equal to the rate at which bromide ion is being added and no further change in the bromide ion content occurs. If the hypochlorite donor/bromide ion donor composition contained the exact amount of bromide ion to compensate for bromide ion losses at the desired steady state, that is the steady state which is eventually attained.

On the other hand, if the tower initially contains an excess of NaBr over the amount required for a Conversion Ratio of 1.0 and a NaBr/ACL mixture is used that corresponds to the desired steady state concentration, the bromide ion loss rate will be higher than the bromide addition rate. In this case, the bromide ion concentration will decrease until the loss rate and addition rate are equal and a steady state at Conversion Ratio=1.0 is reached. Again, this steady state is determined by the bromide ion addition rate, and, if the correct composition is used, the Conversion Ratio will be one at steady state.

This concept can best be visualized by considering the following information. First, in the preceding Example, 11.0 pounds of ACL90 PLUS are required to satisfy the daily chlorine demand of the cooling water. Second, 0.605 lb of sodium bromide are required to maintain the desired Conversion Ratio of 1.0. It follows that the total daily requirements for the hypochlorite donor/bromide ion donor composition, (ACL 90 PLUS/NaBr) are 11.605 pounds (11.0+ 0.605). The appropriate composition of the hypochlorite donor/bromide ion donor composition required to maintain the desired Conversion Ratio is, therefore, 94.8% (11.0/ 11.605×100%=94.8%) ACL90 PLUS and 5.2% (0.605/ 11.605×100%=5.2%) NaBr.

To understand how this composition can build up the bromide ion concentration to the desired level, it is necessary to consider the bromide ion addition rate and total bromide ion loss rate on an hourly basis. Again, as shown above, the total weight of bromide ion, $W_{Br}$, required to maintain the Conversion Ratio at 1.0 was established to be 0.47 lb at steady state. For the purpose of this Example, it is assumed that this will be the total amount of bromide ion that is lost daily. Then the total hourly bromide ion loss rate (all pathways), HTBrL, is simply $W_{Br}$ divided by 24 hours. This corresponds to a rate of 0.01958 lb/hr (0.47 lb÷24 hr=0.01958). With respect to WBr, the percent total hourly bromide ion loss rate, PHTBrL is, as determined by equation (25), 4.2% (0.01958/0.47×100%=4.2%).

$$\text{PHTBrL} = \frac{\text{HTBrL}}{W_{Br}} \times 100\% \quad (25)$$

This percent total hourly loss rate corresponds to a percent total daily loss rate of 100%. It is important to remember that it is entirely possible for percent total daily loss rate to be greater than 100%.

With regards to the bromide ion addition rate, it was established previously that 0.605 lb of sodium bromide are required to satisfy the Conversion Ratio conditions specified. The hourly sodium bromide addition rate is thus 0.02521 lb/hr (0.605 lb÷24 hr). In terms of bromide ion, the total hourly addition rate is 0.01958 lb/hr (0.02521 lb NaBr/hr×$M_{Br}/M_{NaBr}$=0.02521×80/103=0.01958).

It follows that at the end of the first hour of use of the ACL90 PLUS/NaBr composition the bromide ion content of the water will be 0.01958 pounds minus the amount of bromide ion losses. Since the total hourly loss rate is 4.2%/hr, the amount of bromide ion lost in the first hour is only 0.00082 lb (0.042×0.01958). The bromide ion content at the end of the first hour is thus 0.01876 lb (0.01958– 0.00082). At the end of the second hour, another 0.01958 lb of bromide will have been added bringing the gross amount to 0.03834 (0.01876+0.01958) lb. However, the bromide ion loss is slightly higher and amounts to approximately 0.00161 lb (0.03834×0.0420). The net amount of bromide ion remaining has now increased to 0.03673 lb (0.03834– 0.00161). Thus, with each successive addition of sodium bromide, the bromide ion concentration will continue to increase, but at the same time, the bromide ion loss rate will increase. Eventually, the loss rate will catch up with the addition rate and the two rates will be essentially equivalent thereafter. At this point, steady state conditions have been attained and subsequent ACL90 PLUS/NaBr additions merely maintain the Conversion Ratio at the desired level, in this case, 1.0

A further refinement of these calculations is to determine the hourly bromide ion losses by the various pathways, since blowdown losses apply to all bromine species but losses by flashoff of hypobromous acid and bromamines and the formation of organobromine compounds apply only to the hypobromite species. This is achieved with equations (26) and (27). The percent hourly bromide ion loss rate by blowdown, PHBrL(BD), is calculated by equation (26).

$$\text{PHBrL(BD)} = \frac{\text{BrL(BD)}}{C_{Br} \times V_w} \times \frac{1000}{24} \times 100\% \quad (26)$$

where:
PHBrL(BD)=the percent of bromide ion lost by blowdown, %/hr
BrL(BD)=as defined in equation (9)
$C_{Br}$=as defined in step (3) of "calculation of losses method"
$V_w$=volume of recirculating water, L
1000=conversion factor, grams to milligrams
24=conversion factor, days to hours The percent hourly loss of bromide ion by the other pathways (flashoff of hypobromous acid and bromamines and formation of organobromine compounds) is specifically proportional to the amount of hypobromite species in the recirculating water. The percent hourly loss of hypobromite species by these pathways, PHOBrL, is calculated with equation (27).

$$\text{PHOBrL} = \frac{[\text{TBrL} - \text{BrL(BD)}]}{C_{HOBr} \times V_w} \times \frac{M_{HOBr}}{M_{Br}} \times \frac{1000}{24} \times 100\% \tag{27}$$

where:
PHOBrL=percent of hypobromite species lost by pathways other than blowdown, %/hr
TBrL=as defined in equation (23)
BrL(BD)=as defined in equation (9)
$C_{HOBr}$=as defined in step (2) of "calculation of losses method"
$V_W$=volume of recirculating water, L
$M_{HOBr}$=mole weight of hypobromous acid, gm
$M_{Br}$=mole weight of bromide ion, gm
1000=conversion factor, grams to milligrams
24=conversion factor, days to hours
PHOBrL is essentially the weight of hypobromite species lost per hour divided by the weight of hypobromite species contained in the recirculating water. With equation (25), the percent total hourly bromide ion loss rate, PHTBrL, was calculated to be 4.2%/hr. These refinements account for what fraction of bromide ion losses are due to blowdown and the other pathways. To illustrate the refinements of the calculations, the losses due to blowdown, PHBrL(BD), and the losses by other pathways, PHOBrL, are taken to be 0.83%/hr and 3.33%/hr, respectively, for FIGS. 2–5.

These calculations can be used to illustrate the interrelationship between the concentration of the bromide ion in the recirculating water and the composition of the hypochlorite donor/bromide ion donor compositions. They were utilized to generate the graphs shown in FIGS. 2–5 which illustrate the effect of the biocide composition on the buildup of bromide ion with time and the ability of the composition to attain the optimum Conversion Ratio at steady state conditions. Since these calculations simulate the dynamics of the bromide ion content of water recirculation systems, they can be used to determine the composition required to produce the desired Conversion Ratio once the PHBrL(BD) and PHOBrL have been determined. FIG. 6 illustrates the effect of bromide ion loss rate on the composition required for the preferred range of Conversion Ratios. Therefore, it illustrates, in conjunction with the following examples, how the various compositions are able to perform as bromine biocides.

EXAMPLE 9

Figure 2:
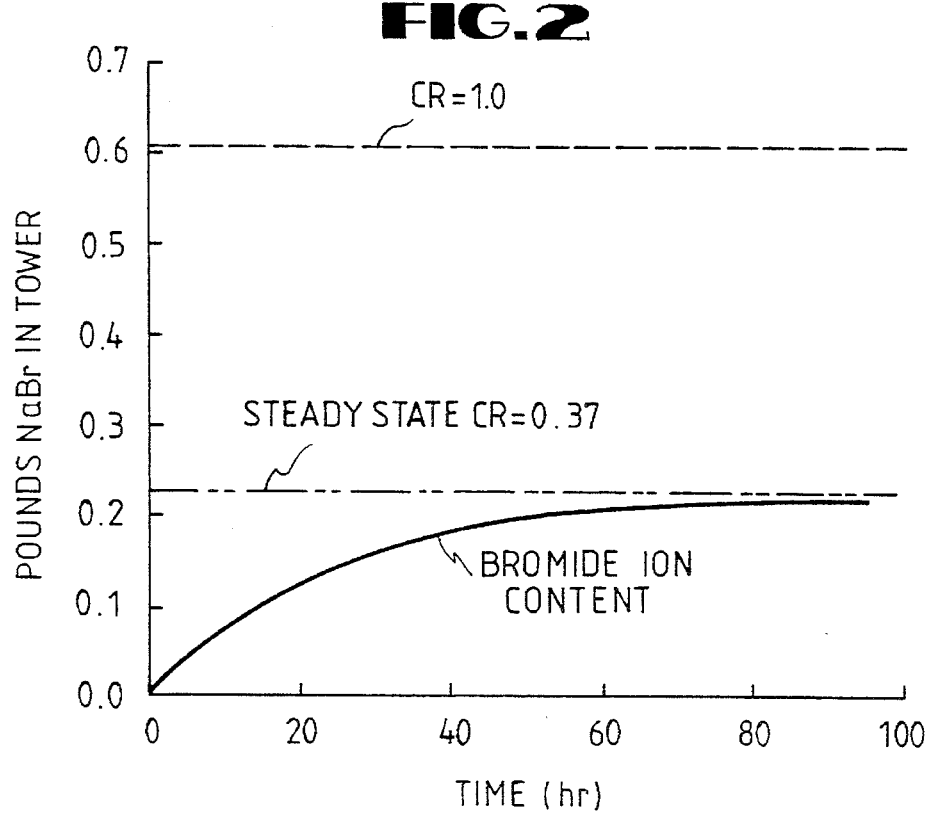
FIGS. 2–6 illustrate the effect of the hypochlorite donor/bromide ion donor composition on the Conversion Ratio in the recirculating water and the ability of the biocide to perform as a bromine biocide. NaBr/ACL90 PLUS and NaBr/ACL60 compositions are used to illustrate the effects.

Buildup of Bromide Ion to Steady State Concentration with a 2% NaBr/98% ACL90 PLUS Composition The cooling tower in Example 8 is initially treated with 11.0 pounds of ACL90 PLUS per day to maintain a free chlorine concentration of 0.5 mg/L, thus the tower initially contains no bromine containing species. The biocide is then switched to a composition of 2% NaBr and 98% ACL90 PLUS. FIG. 2 presents the calculated bromide ion content in terms of sodium bromide of the tower versus the time elapsed since starting the NaBr/ACL90 PLUS composition, given that PHOBrL=3.33%/hour (80%/day) and that PHBrL(BD)=0.83%/hour (20%/day). It shows how the total amount of bromine containing species (given as pounds of NaBr) contained in the recirculating water system builds up with time during the initial few days of use of the 2.0% NaBr/98% ACL90 PLUS composition until a steady state concentration is reached after about three days. At steady state, the tower in FIG. 2 contains about 0.2 pounds of NaBr, which is considerably below the 0.605 pounds of NaBr required for a Conversion Ratio of 1.0, as shown by the line labeled "CR=1.0". In this case, the free halogen is a mixture of hypochlorite species and hypobromite species and the killing efficiency is less than ideal.

EXAMPLE 10

Figure 3:
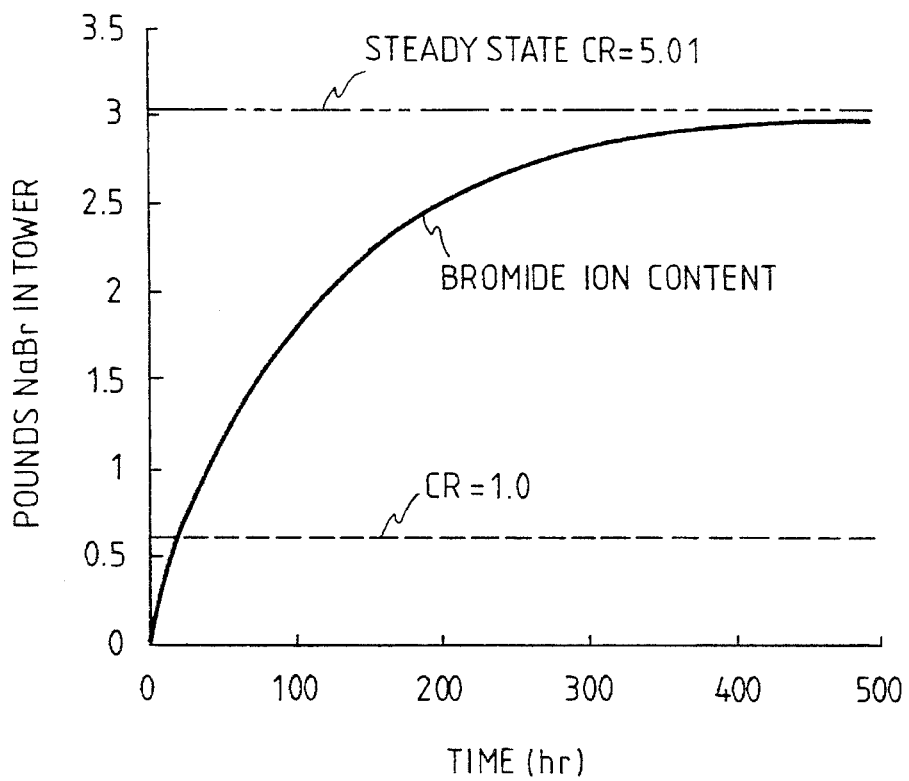

Buildup of Bromide Ion to Steady State Concentration with a 9% NaBr/91% ACL90 PLUS Composition FIG. 3 shows the case where a NaBr/trichloroisocyanuric acid (ACL90 PLUS) composition with a much higher percentage of NaBr (9.0%) is fed into the tower described in Example 8. As in Example 9, the bromide ion content of the tower builds up smoothly until a steady state is reached. In this case, however, steady state is reached in about 20 days. The steady state NaBr content is 3.0 pounds and the steady state Conversion Ratio is 5.0. In this case, all of the free halogen is present as hypobromite species and the killing efficiency is very high, but a considerable excess of bromide ion is present which is wasted.

EXAMPLE 11

Figure 4:
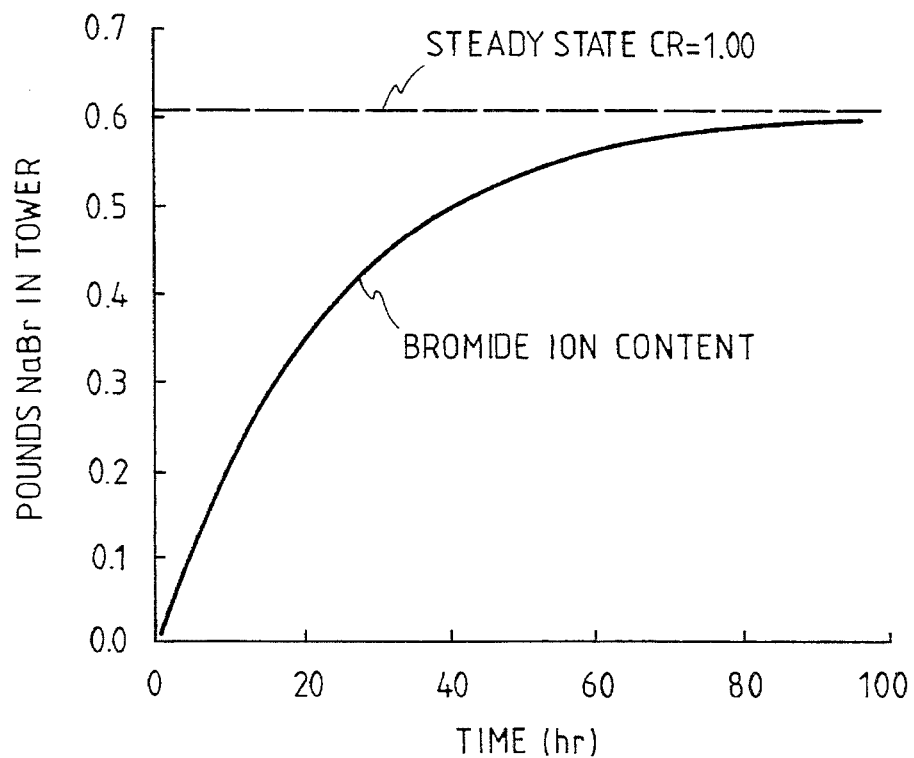

Buildup of Bromide Ion to Steady State Concentration with the Optimum 5.2% NaBr/94.8% ACL90 PLUS Composition FIG. 4 shows the ideal case for the tower described in Example 8, where PHBrL(BD) is 0.83%/hour (20%/day) and PHOBrL is 3.33%/hour (80%/day). A Conversion Ratio of 1.0 is achieved after about three days and then maintained at steady state conditions by feeding a composition of 5.2% NaBr/94.8% trichloroisocyanuric acid. This composition therefore performs as a bromine biocide in this tower with very little excess bromide ion being required.

EXAMPLE 12

Buildup of Bromide Ion to Steady State Concentration with BCDMH

Figure 5:
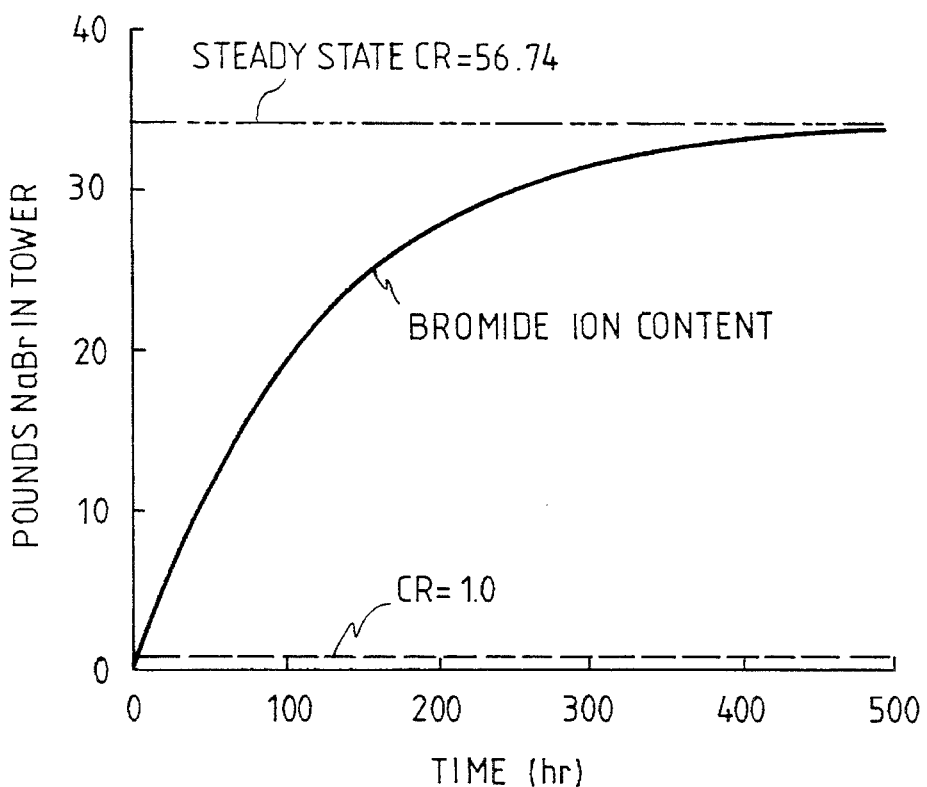
Figure 6:
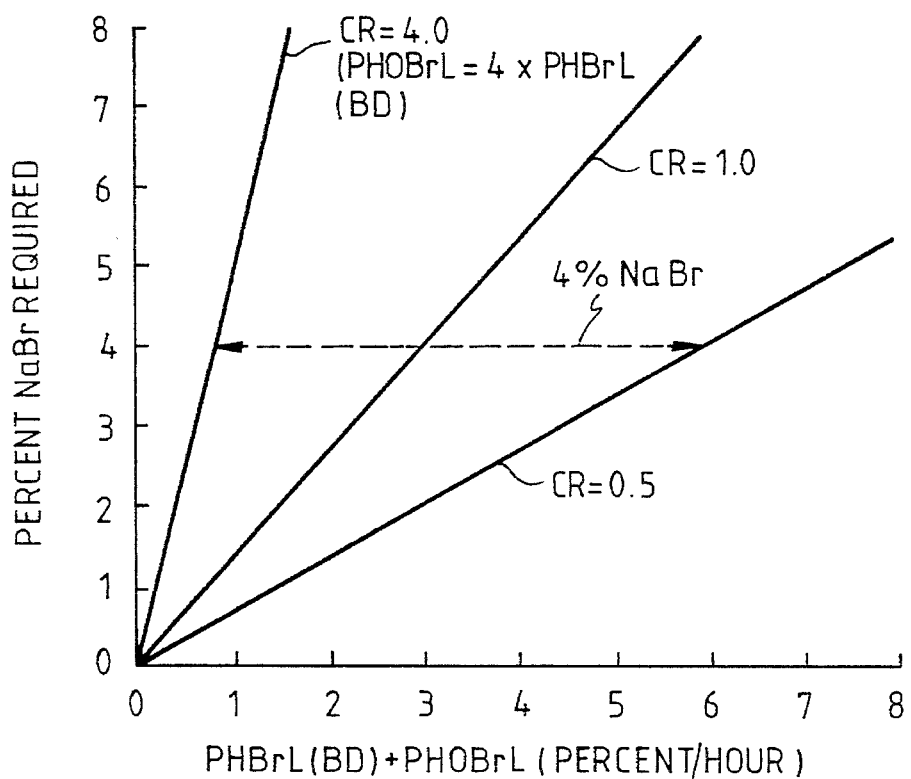

FIG. 5 shows the case for BCDMH, which has a bromide and available halogen content equivalent to about 40% NaBr/60% trichloroisocyanuric acid, in the tower of Example 8. The steady state Conversion Ratio (for PHOBrL=3.33%/hour and PHBrL(BD)=0.83%/hour) which is attained after about 20 days is 56.7. This is a tremendous waste of bromide ion, since 56.7 times as much bromide is used as is necessary to maintain the maximum killing efficiency. This high Conversion Ratio for BCDMH is confirmed by the data in Example 1, Table 1, where a Conversion Ratio of 41.1 was determined experimentally for BCDMH in a tower with somewhat different characteristics. The waste of bromide is even greater for cases where PHOBrL and PHBrL(BD) are lower than used in this example.

EXAMPLE 13

Hypochlorite Donor/Bromide Ion Donor Compositions Required For Specific Steady State Conversion Ratios The relationship between the sum of PHBrL(BD) and PHOBrL and the required composition of a NaBr/trichloroisocyanuric acid (ACL90 PLUS) composition is summarized in FIG. 6. The line labeled 'CR=1.0' gives the relationship between PHBrL(BD)+PHOBrL and the weight % NaBr required in the composition to produce a Conversion Ratio of 1.0. For instance, for a tower with a bromide ion loss rate of 3.3%/hour the NaBr/trichloroisocyanuric acid composition should be 4.8% NaBr. The lines marked 'CR=4.0' and 'CR=0.5' give the relationship for the extremes of the most preferred Conversion Ratio. The dashed arrow at 4% NaBr shows that a composition of 4% NaBr/96% trichloroisocyanuric acid can maintain the Conversion Ratio in the most preferred range of 0.5 to 4.0 for towers for PHBrL(BD)+PHOBrL=0.75%/hour to well over 5%/hour. This range covers virtually all common cooling tower systems. In contrast, a composition with only 2% NaBr/98% trichloroisocyanuric acid will maintain the Conversion Ratio in the most preferred range only for PHBrL(BD)+PHOBrL between 0.38 and 2.5%/hour. Many common cooling towers have larger bromide ion loss rates than this, as was shown in Examples 3 and 4.

This example shows the importance of understanding the relationship between the total bromide ion loss rate and the sodium bromide content of ACL90 PLUS/NaBr compositions and the capabilities of these compositons to attain and maintain the desired Conversion Ratios, especially those that enable these compositions to perform as bromine biocides. These same relationships also exist for other hypochlorite donor/bromide ion donor compositions and/or combinations. These relationships can be established with the methods described herein.

For cooling tower operations subject to EPA discharge limits of 0.2 ppm (available chlorine basis), it is preferred to maintain the Conversion Ratio at or above one, since hypobromite species dissipate faster than hypochlorite species.

For use in air washers, it is preferred that the Conversion Ratio be maintained at or above a value of one since it is important to eliminate all chlorine or chloramine odors from the air passed through the air washer. Odor is more important in air washers than in cooling towers since the washed air is used inside buildings, factories, and the like. Thus, somewhat higher percentages of NaBr are required for compositions of this invention used in cooling tower operations subject to EPA limits and in air washers. For instance, FIG. 6 shows that a 4% NaBr/96% trichloroisocyanuric acid composition will maintain the Conversion Ratio in the preferred range of 1.0 to 4.0 for PHBrL(BD)+PHOBrL= 0.75% to 2.75%/hour. If the loss rate is higher, a composition with a higher NaBr percentage would be necessary.

EXAMPLE 14

Demonstration of Bromide Ion Loss From Spas

This example demonstrates the magnitude of bromide ion loss that can occur in a commercial spa. A spa with a capacity of 1000 gallons of water was chlorinated continuously with ACL90 PLUS (trichloroisocyanuric acid) around the clock to maintain a free chlorine concentration of 2 ppm. The spa water was maintained at a temperature of 40° C. The water was aerated only during the day, the high bather load period, for about 12 hours. Sufficient sodium bromide was added to the spa water to obtain a bromide ion concentration of 3 ppm. This is the amount required to attain a Conversion Ratio of 1.33 versus the optimum of 1.0 and to make the chemicals perform as a bromine sanitizer. Water samples were taken about every four hours for several days. The analyses showed that the bromide ion concentration decreased steadily from 3 to 1 ppm over a period of 6 days. The chlorine demand was about 10 ppm per day (available chlorine basis). During this period, the odor of the air above the spa changed gradually from that of bromamines to chloramines. These results demonstrated that bromide ion was lost from the water and that the hypohalite species were a mixture of hypochlorite and hypobromite species. As a consequence, the biocide performed more like a chlorine sanitizer than a bromine sanitizer.

EXAMPLE 15

Control of Optimum Conversion Ratio in Spas with ACL90 PLUS/NaBr Compositions

This example further demonstrates how knowledge of the bromide ion loss can be applied to the development of the appropriate sanitizer compositions. The results in Example 14 show that the bromide ion loss rate was about 0.33 ppm/day. This means that at least 2.5 grams must be added daily to maintain the desired concentration. The chlorine demand during this period was about 10 ppm/day, which corresponds to a ACL90 PLUS consumption rate of 41.3 grams/day. These results indicate that to satisfy the chlorine demand and bromide ion loss requirements with a product made of the two materials, the product must contain ACL90 PLUS and sodium bromide in the weight proportions of 41.3 to 2.5. Thus, the tablet for this application must contain at least 94.3 wt % ACL90 PLUS and 5.7 wt % sodium bromide.

To demonstrate the utility of this concept, an ACL90 PLUS/sodium bromide mixture with 6% NaBr was compacted into one-inch tablets weighing 15 grams each. The tablets were placed in a standard erosion feeder where the water flow was adjusted to maintain the desired free halogen concentration of 2 ppm (available chlorine basis). Water samples were then taken periodically for six days. The bromide analyses showed that the bromide ion concentration built up steadily to the desired concentration and remained constant for the remainder of the test, thereby insuring that this product was performing as a bromine sanitizer.

Bromine Volatilization Suppressant

It has also been discovered that, in addition to simply adding enough bromide ion donor to compensate for all bromide ion losses, it is possible to approach the problem in a second way, that is, by reducing or suppressing the amount of volatilization of HOBr and bromamines. This can be accomplished by addition of a hypobromous acid volatilization suppressant compound. The volatilization suppressant must bind free bromine species (HOBr) strongly enough to reduce the concentrations of hypobromous acid and bromamine significantly, but not so strongly that the disinfecting properties of the bromine-based biocide will be reduced. In addition, the volatilization suppressant must be chemically compatible with the hypochlorite donor compounds in the single product compositions to be fed to the tower.

Cyanuric acid has been used in swimming pools to reduce the decomposition of hypochlorous acid by the UV rays of sunlight and in cooling towers to reduce the loss of free chlorine. However, cyanuric acid will not suppress the loss of free bromine by volatilization and degradation in sunlight because cyanuric acid does not bind free bromine as strongly as it does free chlorine.

It has been found that hydantoin derivatives (such as DMH); sulfonamide derivatives; sulfamic acid derivatives; glycoluril derivatives; oxazolidinone derivatives; imidazolidinone derivatives; and succinimide derivatives are capable of acting as volatilization suppressants for free bromine. However, it was discovered that when hydantoin derivatives are used, the concentration of the volatilization suppressant relative to the concentration of the free bromine must be controlled in order to avoid significant reduction in the biocidal activity of the biocides of the present invention.

DMH can be used to reduce bromide ion losses by reducing volatilization loss by as much as 85% before it begins to have a deleterious effect on the disinfection properties of the bromine-based biocide according to the present invention. However, DMH concentrations more than ten times the hypobromous acid concentration (expressed in terms of free available chlorine) can significantly decrease the biocidal effectiveness of the hypobromous acid. For example, if the free halogen level in the recirculating water is controlled at 0.5 mg/L (free available chlorine basis), DMH concentrations greater than 5.0 mg/L must be avoided. DMH concentrations of over 50 mg/L can easily be reached if BCDMH is used as the biocide. Because of the potential for reducing the effectiveness of bromine-based biocides, the concentration of DMH or other stabilizer compounds should be maintained at an appropriately low level, preferably less than 10 ppm in the case of DMH.

EXAMPLE 16

Demonstration of the Effect of Dimethylhydantoin on Bromide Ion Losses

This example demonstrates how bromide ion losses can be significantly reduced with bromine volatilization suppressants.

In this particular experiment, the cooling water of Example 4 was dosed with enough sodium bromide to obtain a Conversion Ratio of about one. DMH was then added to the water in an amount sufficient to attain a concentration of 20 ppm. Again, lithium chloride was used as a tracer. The water was recirculated for about one hour to obtain a uniform distribution of chemicals. Water samples were then taken periodically for the next 24 hours and analyzed for bromide, lithium and DMH. The results are tabulated in Table 5.

TABLE 5

Effect of DMH on Bromide Ion Losses

| Water Sample | Time Hr. | Bromide Ion Concentration ppm | DMH Concentration ppm | Lithium Concentration ppm | Bromide Ion Losses (%) |
|---|---|---|---|---|---|
| 1 | 1 | 0.5 | 21 | 0.45 | 0 |
| 2 | 2 | 0.5 | 20 | 0.44 | 0 |
| 3 | 3 | 0.5 | 19 | 0.42 | 0 |
| 4 | 4 | 0.48 | 20 | 0.42 | 4 |
| 5 | 8 | 0.46 | 20 | 0.42 | 8 |
| 6 | 16 | 0.42 | 19 | 0.41 | 18 |
| 7 | 24 | 0.38 | 18 | 0.42 | 24 |

These data demonstrate that bromide ion losses were reduced dramatically with the addition of DMH, thus establishing another way to compensate for bromide ion losses via the volatilization pathway.

EXAMPLE 17

Effect of DMH on Henry's Law Constants for Hypobromous Acid

The previous example demonstrated that DMH could be used to obtain significant reductions in bromide ion losses from cooling water systems containing the hypochlorite donor/bromide ion donor compositions described in this invention. This example shows the effect of the DMH concentration on the tendency of the bromide ion to be lost from cooling waters by volatilization. Just as important, it provides data critical to controlling the DMH concentration so that the excellent biocidal properties of these bromine biocide compositions are not compromised by high DMH residuals.

The effect of DMH concentration was demonstrated by determining the Henry's Law constants for a series of solutions in which the available halogen, bromide, pH and temperature were held constant but the DMH concentration was varied.

Figure 7:
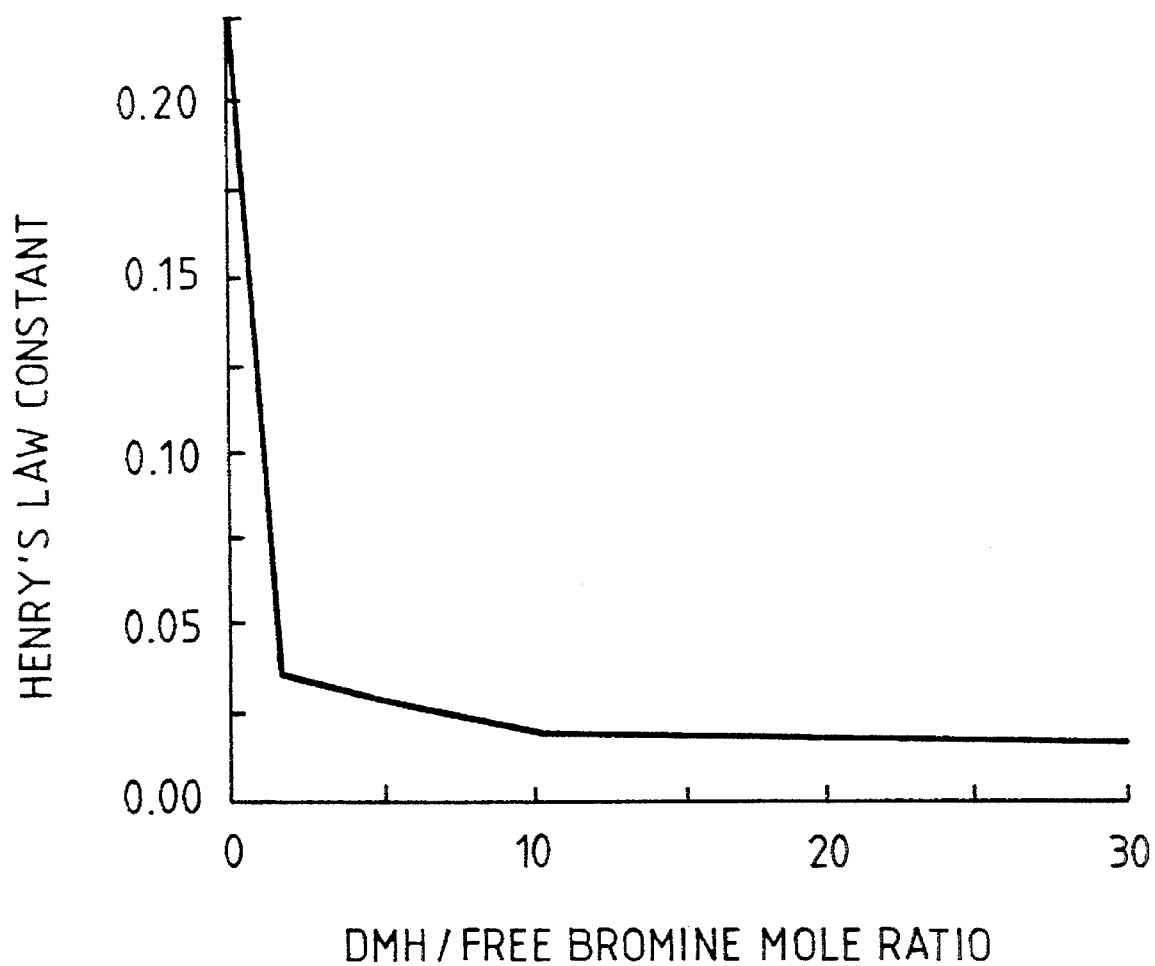
FIG. 7 illustrates the effect of DMH on the Henry's Law constant for a bromine biocide.

The results of these experiments are tabulated in Table 6 and shown graphically in FIG. 7.

TABLE 6

Effect of DMH on Henry's Law Constants For
Solutions Containing Hypohalite Species and
Bromide Ion Experimental Conditions pH = 8.5
Temperature = 22.5° C.
Free halogen (as $Cl_2$) = 2 mg/L
Bromide ion = 2.25 mg/L

| DMH/Free Bromine Mole Ratio | Henry's Law Constant $H_k$ |
|---|---|
| 0.0 | 0.220 |
| 2.0 | 0.037 |
| 5.0 | 0.028 |
| 10.0 | 0.024 |
| 30.0 | 0.019 |

Depicting these results graphically, FIG. 7 shows that the

Henry's Law constant decreased significantly as the DMH/free bromine mole ratio increased from 0 to 10, but decreased very little above 10. These results indicate that there is no need to use DMH/free bromine ratios of greater than 10. More importantly, killing efficiency data show that the biocidal properties begin to decrease significantly above this ratio.

The foregoing description has been directed to particular embodiments of the invention for the purposes of illustration and explanation. It will be apparent, however, to those skilled in this art that many modifications and changes in the compositions and methods set forth will be possible without departing from the scope and spirit of the invention. It is intended that the following claims be interpreted to embrace all such modifications and changes.

What is claimed is:

1. A biocidal composition for use in recirculating water systems comprising a hypochlorite donor and a bromide ion donor, wherein the composition contains a biocidally effective amount of the bromide ion donor to make the composition perform as a bromine biocide in said recirculating water system and to maintain a mole ratio of the sum of all bromine containing species to the sum of all hypohalite species in the recirculating water of at least about 0.2 to about 20; and wherein the hypochlorite donor is dichloroisocyanuric acid, trichloroisocyanuric acid, or mixtures thereof; and wherein the bromide ion donor is sodium bromide.

2. The composition of claim 1 wherein the hypochlorite donor is trichloroisocyanuric acid and the bromide ion donor is sodium bromide.

3. The composition of claim 1 wherein the hypochlorite donor is dichloroisocyanuric acid and the bromide ion donor is sodium bromide.

4. The composition of claim 1, 2, or 3 comprising:

from about 85 parts by weight to about 99 parts by weight of the hypochlorite donor; and from about 1 part by weight to about 15 parts by weight of the bromide ion donor.

5. A biocidal composition for use in recirculating water systems comprising a hypochlorite donor and a bromide ion donor, wherein the composition contains a biocidally effective amount of the bromide ion donor to maintain a mole ratio of the sum of all bromine containing species to the sum of all hypohalite species in the recirculating water of about 0.2 to about 20; and wherein the hypochlorite donor is trichloroisocyanuric acid and the bromide ion donor is a N-brominated hydantoin.

6. A biocidal composition for use in recirculating water systems comprising a hypochlorite donor and a bromide ion donor, wherein the composition contains a biocidally effective amount of the bromide ion donor to maintain a mole ratio of the sum of all bromine containing species to the sum of all hypohalite species in the recirculating water of about 0.2 to about 20; and wherein the hypochlorite donor is trichloroisocyanuric acid and the bromide ion donor is a bromochlorohydantoin.

7. A biocidal composition for use in recirculating water systems comprising a hypochlorite donor and a bromide ion donor, wherein the composition contains a biocidally effective amount of the bromide ion donor to maintain a mole ratio of the sum of all bromine containing species to the sum of all hypohalite species in the recirculating water of about 0.2 to about 20; and wherein the hypochlorite donor is a dichlorohydantoin and the bromide ion donor is a bromochlorohydantoin.

8. The composition of claim 5, 6, or 7 comprising from about 50 parts by weight to about 99 parts by weight hypochlorite donor; and from about 1 parts by weight to about 50 parts by weight bromide ion donor.

9. A solid biocidal composition for controlling biofouling and microorganism population levels in recirculating water systems that provides hypobromous acid when immersed in water, comprising a hypochlorite donor and a bromide ion donor in amounts sufficient to make said composition perform as a bromine biocide in said recirculating water system:

(i) wherein said hypochlorite donor is selected from the group consisting of trichloro-s-triazinetrione, dichloroisocyanuric acid, or mixtures thereof; and (ii) said bromide ion donor is sodium bromide.

10. The biocidal composition according to claim 9 wherein said biocidal composition is compacted into tablets, sticks or pucks; said hypochlorite donor is trichloro-s-triazinetrione; and said bromide ion donor is sodium bromide.

11. The biocidal composition according to claim 9 wherein said biocidal composition is compacted into tablets, sticks or pucks; said hypochlorite donor is dichloroisocyanuric acid; and said bromide ion donor is sodium bromide.

12. The biocidal composition according to claim 9, 10 or 11 comprising (i) from about 85 to about 99 parts by weight of said hypochlorite donor; and (ii) from about 1 to about 15 parts by weight of said bromide ion donor.

13. The biocidal composition according to claim 9 further comprising a bromine volatilization suppressant selected from the group consisting of 5,5-dimethylhydantoin or glycoluril.

14. The biocidal composition according to claim 13 wherein said solid composition is compacted into tablets, sticks or pucks; said hypochlorite donor is trichloro-s-triazinetrione or dichloroisocyanuric acid; said bromide ion donor is sodium bromide; and said bromine volatilization suppressant is 5,5-dimethylhydantoin.

15. The biocidal composition according to claim 13 wherein said solid composition is compacted into tablets, sticks or pucks; said hypochlorite donor is trichloro-s-triazinetrione or dichloroisocyanuric acid; said bromide ion donor is sodium bromide; and said bromine volatilization suppressant is glycoluril.

16. The biocidal composition according to claim 13, 14, or 15 comprising (i) from about 85 to about 98 parts by weight of said hypochlorite ion donor;

(ii) from about 1 to about 15 parts by weight of said bromide ion donor; and (iii) from about 1 to about 10 parts by weight of said volatilization suppressant.

17. A solid biocidal composition for controlling biofouling and microorganism population levels in recirculating water systems that provides hypobromous acid when immersed in water, comprising a hypochlorite donor and a bromide ion donor in amounts sufficient to make said composition perform as a bromine biocide in said recirculating water system:

(i) wherein said hypochlorite donor is selected from the group consisting of trichloro-s-triazinetrione, dichloroisocyanuric acid, [mono(trichloro)-tetra(monopotassium dichloro)]-penta-s-triazinetrione, [mono(trichloro)-mono(monopotassium dichloro)]-di-s-triazinetrione, or mixtures thereof; and (ii) said bromide ion donor is an N-brominated hydantoin.

18. The biocidal composition according to claim 17 wherein said biocidal composition is compacted into tablets, sticks or pucks; said hypochlorite donor is trichloro-s-triazinetrione; and said bromide ion donor is a bromochlorohydantoin.

19. The biocidal composition according to claim 17 wherein said solid composition is compacted into tablets, sticks or pucks; said hypochlorite donor is dichloroisocyanuric acid; and said bromide ion donor is a bromochlorohydantoin.

20. The biocidal composition according to claim 17 further comprising a bromine volatilization suppressant compound selected from the group consisting of 5,5-dimethylhydantoin or glycoluril.

21. A solid biocidal composition for use in recirculating water systems comprising a hypochlorite donor and a bromide ion donor:

(i) wherein said hypochlorite donor is selected from the group consisting of trichloro-s-triazinetrione, dichloroisocyanuric acid, or mixtures thereof; and (ii) said bromide ion donor is sodium bromide.

22. The biocidal composition according to claim 21 wherein said biocidal composition is compacted into tablets, sticks or pucks; said hypochlorite donor is trichloro-s-triazinetrione; and said bromide ion donor is sodium bromide.

23. The biocidal composition according to claim 21 wherein said biocidal composition is compacted into tablets, sticks or pucks; said hypochlorite donor is dichloroisocyanuric acid; and said bromide ion donor is sodium bromide.

24. The biocidal composition according to claim 21, 22 or 23 comprising (i) from about 85 to about 99 parts by weight of said hypochlorite donor; and (ii) from about 1 to about 15 parts by weight of said bromide ion donor.

25. The biocidal composition according to claim 21 further comprising a bromine volatilization suppressant selected from the group consisting of 5,5-dimethylhydantoin or glycoluril.

26. The biocidal composition according to claim 25 wherein said solid composition is compacted into tablets, sticks or pucks; said hypochlorite donor is trichloro-s-triazinetrione or dichloroisocyanuric acid; said bromide ion donor is sodium bromide; and said bromine volatilization suppressant is 5,5-dimethylhydantoin.

27. The biocidal composition according to claim 25 wherein said solid composition is compacted into tablets, sticks or pucks; said hypochlorite donor is trichloro-s-triazinetrione or dichloroisocyanuric acid; said bromide ion donor is sodium bromide; and said bromine volatilization suppressant is glycoluril.

28. The biocidal composition according to claim 25, 26, or 27 comprising (i) from about 85 to about 98 parts by weight of said hypochlorite ion donor;

(ii) from about 1 to about 15 parts by weight of said bromide ion donor; and (iii) from about 1 to about 10 parts by weight of said volatilization suppressant.

29. A solid biocidal composition for use in recirculating water systems, comprising a hypochlorite donor and a bromide ion donor:

(i) wherein said biocidal composition contains a biocidally effective amount of the bromide ion donor in amounts sufficient to make said composition perform as a bromine biocide in said recirculating water system and to maintain a mole ratio of the sum of all bromine containing species to the sum of all hypohalite species in the recirculating water of about 0.2 to about 20;

(ii) wherein said hypochlorite donor is selected from the group consisting of trichloro-s-triazinetrione, dichloroisocyanuric acid, [mono(trichloro)-tetra(monopotassium dichloro)]-penta-s-triazinetrione, [mono(trichloro)-mono(monopotassium dichloro)]-di-s-triazinetrione, or mixtures thereof; and (iii) said bromide ion donor is an N-brominated hydantoin.

30. The biocidal composition according to claim 29 wherein said biocidal composition is compacted into tablets, sticks or pucks; said hypochlorite donor is trichloro-s-triazinetrione; and said bromide ion donor is a bromochlorohydantoin.

31. The biocidal composition according to claim 29 wherein said solid composition is compacted into tablets, sticks or pucks; said hypochlorite donor is dichloroisocyanuric acid; and said bromide ion donor is a bromochlorohydantoin.

32. The biocidal composition according to claim 29 further comprising a bromine volatilization suppressant compound selected from the group consisting of 5,5-dimethylhydantoin or glycoluril.

33. A method of controlling biofouling and microorganism population levels in a recirculating water system comprising (a) determining the rate of loss of bromide ion from the system due to blow-down, volatilization and formation of stable organobromine compounds; and (b) adding, in a biocidally effective amount to provide prolonged and controlled release of hypobromous acid and to maintain the mole ratio of the sum of all bromine containing species to the sum of all hypohalite species in the recirculating water in the range of at least about 0.2 to about 20, a solid biocidal composition comprising a hypochlorite donor and a bromide ion donor in amounts sufficient to make said composition perform as a bromine biocide in said recirculating water system, (i) wherein said hypochlorite donor is selected from the group consisting of trichloro-s-triazinetrione, dichloroisocyanuric acid, or mixtures thereof; and (ii) wherein said bromide ion donor is sodium bromide.

34. The method according to claim 33 wherein said biocidal composition is compacted into tablets, sticks or pucks; said hypochlorite donor is trichloro-s-triazinetrione; and said bromide ion donor is sodium bromide.

35. The method according to claim 33 wherein said biocidal composition is compacted into tablets, sticks or pucks; said hypochlorite donor is dichloroisocyanuric acid; and said bromide ion donor is sodium bromide.

36. The method according to claim 33, 34, or 35, wherein said biocidal composition comprises (i) from about 85 to about 99 parts by weight of said hypochlorite donor; and (ii) from about 1 to about 15 parts by weight of said bromide ion donor.

37. The method according to claim 33 wherein said biocidal composition further comprises a bromine volatilization suppressant selected from the group consisting of 5,5-dimethylhydantoin or glycoluril.

38. The method according to claim 37 wherein said biocidal composition is compacted into tablets, sticks or pucks; said hypochlorite donor is trichloro-s-triazinetrione or dichloroisocyanuric acid; said bromide ion donor is sodium bromide; and said bromine volatilization suppressant is 5,5-dimethylhydantoin.

39. The method according to claim 37 wherein said biocidal composition is compacted into tablets, sticks or pucks; said hypochlorite donor is trichloro-s-triazinetrione or dichloroisocyanuric acid; said bromide ion donor is sodium bromide; and said bromine volatilization suppressant compound is glycoluril.

40. The method according to claim 37, 38, or 39 wherein said biocidal composition comprises (i) from about 85 to about 98 parts by weight of said hypochlorite ion donor;

(ii) from about 1 to about 15 parts by weight of said bromide ion donor; and (iii) from about 1 to about 10 parts by weight of said volatilization suppressant.

41. A method of providing prolonged and controlled release of hypobromous acid in a recirculating water system in a biocidally effective amount to maintain the mole ratio of the sum of all bromine containing species to the sum of all hypohalite species in the recirculating water in the range of at least about 0.2 to about 20, comprising (i) determining the rate of loss of bromide ion from the system due to blow-down, volatilization and formation of stable organobromine compounds; and (ii) adding to the system a solid biocidal composition comprising a hypochlorite donor and a bromide ion donor in amounts sufficient to make said composition perform as a bromine biocide in said recirculating water system;

(iii) wherein said hypochlorite donor is selected from the group consisting of trichloro-s-triazinetrione, dichloroisocyanuric acid, or mixtures thereof; and (iv) wherein said bromide ion donor is sodium bromide.

42. A method of maintaining the bromine concentration in a recirculating water system in a mole ratio of the sum of all bromine containing species to the sum of all hypohalite species in a recirculating water system in the range of at least about 0.2 to about 20 comprising:

(i) determining the rate of loss of bromide ion from the system due to blow-down, volatilization and formation of stable organobromine compounds; and (ii) adding to the system a solid composition comprising a hypochlorite donor and a bromide ion donor in amounts sufficient to make said composition perform as a bromine biocide in said recirculating water system;

(iii) wherein said hypochlorite donor is selected from the group consisting of trichloro-s-triazinetrione, dichloroisocyanuric acid, or mixtures thereof; and (iv) wherein said bromide ion donor is sodium bromide.

43. The biocidal composition according to claim 1, 5–8, 9, 17, 21, or 29, further comprising a bromine volatilization suppressant selected from the group consisting of unsubstituted, halogenated or alkylated hydantoin; unsubstituted, halogenated or alkylated sulfonamide; unsubstituted, halogenated or alkylated sulfamic acid; unsubstituted, halogenated or alkylated glycoluril; unsubstituted, halogenated or alkylated succinimide; unsubstituted, halogenated or alkylated oxazolidinone; or unsubstituted, halogenated or alkylated imidazolidinone.

44. The biocidal composition according to claim 43 further comprising a compacting aid.

45. The biocidal composition according to claim 44, wherein the compacting aid is one or more of boric acid, sodium stearate, potassium stearate, aluminum hydroxide, or monoglycerol stearate.

46. A method of controlling biofouling and microorganism population levels in a recirculating water system comprising (a) determining the rate of loss of bromide ion from the system due to blow-down, volatilization and formation of stable organobromine compounds; and (b) adding, in a biocidally effective amount to provide prolonged and controlled release of hypobromous acid and to maintain the mole ratio of the sum of all bromine containing species to the sum of all hypohalite species in the recirculating water in the range of at least about 0.2 to about 20, a solid biocidal composition comprising a hypochlorite donor and a bromide ion donor in amounts sufficient to make said composition perform as a bromine biocide in said recirculating water system, (i) wherein said hypochlorite donor is selected from the group consisting of trichloro-s-triazinetrione, dichloroisocyanuric acid, [mono(trichloro)-tetra(monopotassium dichloro)]-penta-s-triazinetrione, [mono(trichloro)-mono(monopotassiumdichloro)]-di-s-triazinetrione, or mixtures thereof; and (ii) wherein said bromide ion donor is an N-brominated hydantoin.

47. The method according to claim 46, wherein the bromide ion donor is a bromochlorohydantoin.

48. The method according to claim 46 wherein said biocidal composition comprises:

from about 50 parts by weight to about 99 parts by weight hypochlorite donor; and from about 1 part by weight to about 50 parts by weight bromide ion donor.

49. The method according to claim 33 or 46, wherein said biocidal composition further comprises a bromine volatilization suppressant selected from the group consisting of unsubstituted, halogenated or alkylated hydantoin; unsubstituted, halogenated or alkylated sulfonamide; unsubstituted, halogenated or alkylated sulfamic acid; unsubstituted, halogenated or alkylated glycoluril; unsubstituted, halogenated or alkylated succinimide; unsubstituted, halogenated or alkylated oxazolidinone; or unsubstituted, halogenated or alkylated imidazolidinone.

50. The method according to claim 49, wherein said biocidal composition further comprises a compacting aid.

51. The method according to claim 50, wherein the compacting aid is one or more of boric acid, sodium stearate, potassium stearate, aluminum hydroxide, or monoglycerol stearate.

52. The method according to claim 33, 41, 42, and 46, wherein said biocidal composition is introduced into the recirculating water system by any of the following means: an erosion feeder, a floater, porous bags, perforated buckets or hand dosing.

53. The biocidal composition according to claim 43 wherein said bromine volatilization suppressant is selected from the group consisting of unsubstituted, halogenated or alkylated hydantoin or unsubstituted, halogenated or alkylated glycoluril.

54. The biocidal composition according to claim 53 wherein said bromine volatilization suppressant is halogenated dimethylhydantoin or halogenated glycoluril.

55. The biocidal composition according to claim 54 wherein said bromine volatilization suppressant is chlorinated or brominated dimethylhydantoin.

56. The biocidal composition according to claim 54 wherein said bromine volatilization suppressant is chlorinated or brominated glycoluril.

57. A method of providing biocidal control in a recirculating water system comprising adding to the recirculating water system a hypochlorite donor and a bromide ion donor, wherein the hypochlorite donor is dichloroisocyanuric acid, trichloro-s-triazinetrione, [mono(trichloro)-tetra-(monopotassium dichloro)]-penta-s-triazinetrione, [mono(trichloro)-mono(monopotassium dichloro)]-di-s-triazinetrione, or mixtures thereof; and wherein the bromide ion donor is sodium bromide.

58. The method according to claim 57 wherein said hypochlorite donor is trichloro-s-triazinetrione; and said bromide ion donor is sodium bromide.

59. The method according to claim 57 wherein said hypochlorite donor is dichloroisocyanuric acid; and said bromide ion donor is sodium bromide.

60. The method according to claim 57, 58 or 59 comprising adding (i) from about 85 to about 99 parts by weight of said hypochlorite donor; and (ii) from about 1 to about 15 parts by weight of said bromide ion donor.

61. The method according to claim 57, further comprising adding a bromine volatilization suppressant selected from the group consisting of unsubstituted, halogenated or alkylated hydantoin; unsubstituted, halogenated or alkylated sulfonamide; unsubstituted, halogenated or alkylated sulfamic acid; unsubstituted, halogenated or alkylated glycoluril; unsubstituted, halogenated or alkylated succinimide; unsubstituted, halogenated or alkylated oxazolidinone; or unsubstituted, halogenated or alkylated imidazolidinone.

62. The method according to claim 61 wherein said bromine volatilization suppressant is selected from the group consisting of unsubstituted, halogenated or alkylated hydantoin or unsubstituted, halogenated or alkylated glycoluril.

63. The method according to claim 62 wherein said bromine volatilization suppressant is halogenated dimethylhydantoin or halogenated glycoluril.

64. The method according to claim 63 wherein said bromine volatilization suppressant is chlorinated or brominated dimethylhydantoin.

65. The method according to claim 64 wherein said bromine volatilization suppressant is chlorinated or brominated glycoluril.

66. The method according to claim 61, 62, 63, 64 or 65 comprising adding (i) from about 85 to about 98 parts by weight of said hypochlorite ion donor;

(ii) from about 1 to about 15 parts by weight of said bromide ion donor; and (iii) from about 1 to about 10 parts by weight of said volatilization suppressant.

67. A method of providing biocidal control in a recirculating water system comprising adding to the recirculating water system a hypochlorite donor and a bromide ion donor, wherein the hypochlorite donor is dichloroisocyanuric acid, trichloro-s-triazinetrione, [mono(trichloro)-tetra-(monopotassium dichloro)]-penta-s-triazinetrione, [mono(trichloro)-mono(monopotassium dichloro)]-di-s-triazinetrione, or mixtures thereof; and wherein the bromide ion donor is a N-brominated hydantoin.

68. The method according to claim 67, wherein the bromide ion donor is a bromochlorohydantoin.

69. A method of providing biocidal control in a recirculating water system comprising adding to the recirculating water system a hypochlorite donor and a bromide ion donor, wherein the hypochlorite donor is dichlorohydantoin; and wherein the bromide ion donor is a N-brominated hydantoin.

70. The method according to claim 67, 68 or 69, comprising adding from about 50 parts by weight to about 99 parts by weight of said hypochlorite donor; and from about 1 parts by weight to about 50 parts by weight of said bromide ion donor.

71. The method according to claim 67, further comprising adding a bromine volatilization suppressant compound selected from the group consisting of dimethylhydantoin or glycoluril.

* * * * *